(12) United States Patent
Deinhammer et al.

(10) Patent No.: US 9,677,095 B2
(45) Date of Patent: Jun. 13, 2017

(54) PROCESSES FOR PRODUCING FERMENTATION PRODUCTS

(71) Applicant: NOVOZYMES A/S, Bagsvaerd (DK)

(72) Inventors: Randall Deinhammer, Wake Forest, NC (US); Anne Glud Hjulmand, Snekkersten (DK); Joyce Craig, Pittsboro, NC (US); Guillermo Coward-Kelly, Wake Forest, NC (US); Tomoko Matsui, Chiba (JP); Shinobu Takagi, Chiba (JP); Suzanne Clark, Youngsville, NC (US); John Matthews, Louisberg, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/351,471

(22) PCT Filed: Oct. 9, 2012

(86) PCT No.: PCT/US2012/059335
§ 371 (c)(1),
(2) Date: Apr. 11, 2014

(87) PCT Pub. No.: WO2013/055676
PCT Pub. Date: Apr. 18, 2013

(65) Prior Publication Data
US 2014/0273135 A1    Sep. 18, 2014

Related U.S. Application Data

(60) Provisional application No. 61/566,165, filed on Dec. 2, 2011, provisional application No. 61/545,865, filed on Oct. 11, 2011.

(51) Int. Cl.
| | |
|---|---|
| *C12P 7/14* | (2006.01) |
| *C12P 7/06* | (2006.01) |
| *C12N 9/28* | (2006.01) |
| *C12N 9/30* | (2006.01) |
| *C12N 9/34* | (2006.01) |
| *C12N 9/58* | (2006.01) |

(52) U.S. Cl.
CPC ............ *C12P 7/14* (2013.01); *C12N 9/242* (2013.01); *C12N 9/2417* (2013.01); *C12N 9/2428* (2013.01); *C12N 9/58* (2013.01); *C12P 7/06* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 2006/0148054 A1* | 7/2006 | Fukuyama | ............ C12N 9/242 435/161 |
| 2008/0009049 A1 | 1/2008 | Viksoe-Nielsen et al. | |
| 2009/0117642 A1 | 5/2009 | Power et al. | |

FOREIGN PATENT DOCUMENTS

| | | | | |
|---|---|---|---|---|
| DK | 10 2005 062984 A1 | 7/2007 | | |
| WO | WO 9919467 A1 * | 4/1999 | ............ | C11D 3/386 |
| WO | 2004/113551 A1 | 12/2004 | | |
| WO | 2007144424 A2 | 12/2007 | | |
| WO | WO 2010008841 A2 * | 1/2010 | | |
| WO | 2011082425 A2 | 7/2011 | | |
| WO | 2011/100161 A1 | 8/2011 | | |
| WO | 2011127820 A1 | 10/2011 | | |
| WO | WO 2011127802 A1 * | 10/2011 | | |

OTHER PUBLICATIONS

Berg, JM et al. Biochemistry Fifth Edition, W.H. Freeman and Company, New York, pp. 176-177.*
De Souza et al, 2010, Brazilian J Microbiol 41, 850-861.
Fukuda et al, 2009, Biochem Eng J 44, 2-12.
Prakash, Appl Biochem Biotechnol 160, 2401-2414.
Sun et al, 2010, Appl Biochem Biotechnol 160, 988-1003.
Tawil et al, 2011, Biomacromolecules 12, 34-42.

\* cited by examiner

*Primary Examiner* — Paul Holland
(74) *Attorney, Agent, or Firm* — David Fazzolare

(57) ABSTRACT

The present invention relates to processes for producing fermentation products from starch-containing material, wherein a bacterial alpha-amylase, a raw starch hydrolyzing alpha-amylase and a carbohydrate-source generating enzyme are present and/or added during liquefaction. The invention also relates to compositions suitable for use in processes of the invention.

16 Claims, 1 Drawing Sheet

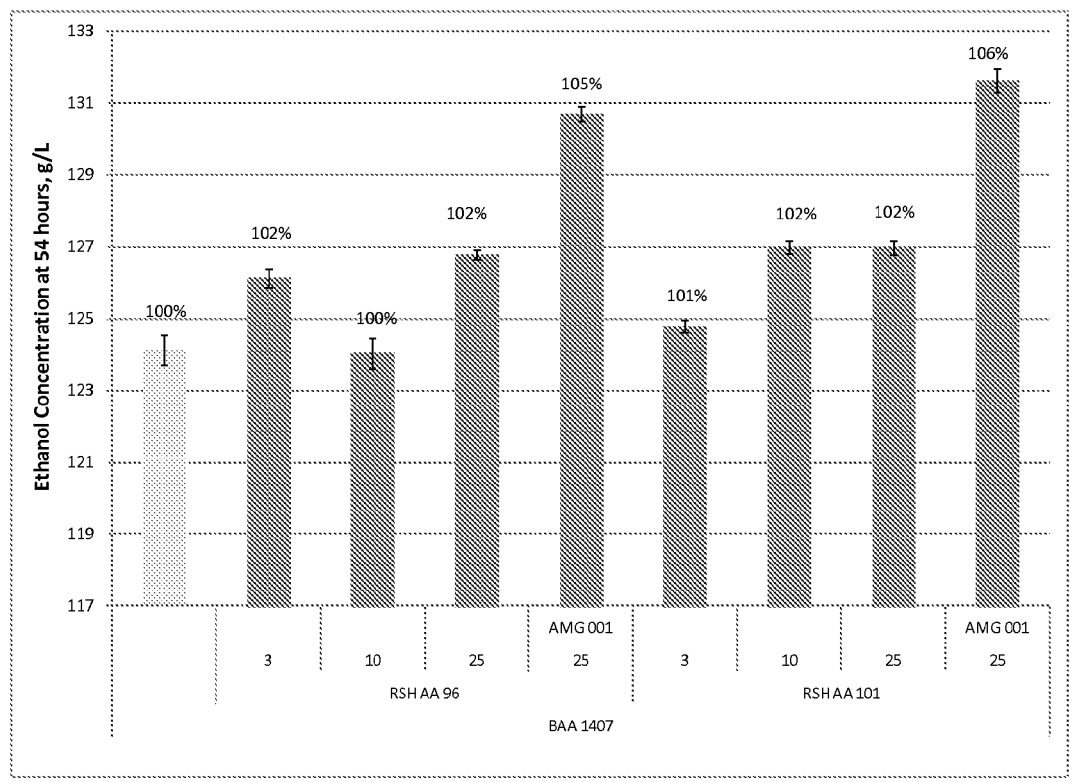

SEQUENCE LISTING

<160> NUMBER OF SEQ ID NOS: 16

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

```
Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2 atg cgg ctc gtt  gct tcc cta acg  gcc ttg gtg gcc  ttg tcc gta        45
Met Arg Leu Val  Ala Ser Leu Thr  Ala Leu Val Ala  Leu Ser Val
            -175                 -170             -165 cct gtc ttt ccc  gct gct gtc aac  gtg aag cgt gct  tcg tcc tac        90
Pro Val Phe Pro  Ala Ala Val Asn  Val Lys Arg Ala  Ser Ser Tyr
        -160                 -155                 -150 ctg gag atc act  ctg agc cag gtc  agc aac act ctg  atc aag gcc       135
Leu Glu Ile Thr  Leu Ser Gln Val  Ser Asn Thr Leu  Ile Lys Ala
            -145                 -140             -135 gtg gtc cag aac  act ggt agc gac  gag ttg tcc ttc  gtt cac ctg       180
Val Val Gln Asn  Thr Gly Ser Asp  Glu Leu Ser Phe  Val His Leu
        -130                 -125                 -120 aac ttc ttc aag  gac ccc gct cct  gtc aaa aag gta  tcg gtc tat       225
Asn Phe Phe Lys  Asp Pro Ala Pro  Val Lys Lys Val  Ser Val Tyr
    -115                 -110                 -105 cgc gat ggg tct  gaa gtg cag ttc  gag ggc att ttg  agc cgc tac aaa   273
Arg Asp Gly Ser  Glu Val Gln Phe  Glu Gly Ile Leu  Ser Arg Tyr Lys
        -100                 -95                  -90 tcg act ggc ctc  tct cgt gac gcc  ttt act tat ctg  gct ccc gga gag   321
Ser Thr Gly Leu  Ser Arg Asp Ala  Phe Thr Tyr Leu  Ala Pro Gly Glu
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | -85 |     |     |     | -80 |     |     |     |     | -75 |     |     |     |     |
| tcc | gtc | gag | gac | gtt | ttt | gat | att | gct | tcg | act | tac | gat | ctg | acc | agc | 369 |
| Ser | Val | Glu | Asp | Val | Phe | Asp | Ile | Ala | Ser | Thr | Tyr | Asp | Leu | Thr | Ser |
|     | -70 |     |     |     | -65 |     |     |     |     | -60 |     |     |     |     |     |
| ggc | ggc | cct | gta | act | atc | cgt | act | gag | gga | gtt | gtt | ccc | tac | gcc | acg | 417 |
| Gly | Gly | Pro | Val | Thr | Ile | Arg | Thr | Glu | Gly | Val | Val | Pro | Tyr | Ala | Thr |
| -55 |     |     |     |     | -50 |     |     |     |     | -45 |     |     |     |     | -40 |
| gct | aac | agc | act | gat | att | gcc | ggc | tac | atc | tca | tac | tcg | tct | aat | gtg | 465 |
| Ala | Asn | Ser | Thr | Asp | Ile | Ala | Gly | Tyr | Ile | Ser | Tyr | Ser | Ser | Asn | Val |
|     |     |     | -35 |     |     |     |     | -30 |     |     |     |     | -25 |     |     |
| ttg | acc | att | gat | gtc | gat | ggc | gcc | gct | gct | gcc | act | gtc | tcc | aag | gca | 513 |
| Leu | Thr | Ile | Asp | Val | Asp | Gly | Ala | Ala | Ala | Ala | Thr | Val | Ser | Lys | Ala |
|     |     | -20 |     |     |     |     | -15 |     |     |     |     | -10 |     |     |     |
| atc | act | cct | ttg | gac | cgc | cgc | act | agg | atc | agt | tcc | tgc | tcc | ggc | agc | 561 |
| Ile | Thr | Pro | Leu | Asp | Arg | Arg | Thr | Arg | Ile | Ser | Ser | Cys | Ser | Gly | Ser |
|     | -5  |     |     |     |     | -1  | 1   |     |     |     | 5   |     |     |     |     |
| aga | cag | agc | gct | ctt | act | acg | gct | ctc | aga | aac | gct | gct | tct | ctt | gcc | 609 |
| Arg | Gln | Ser | Ala | Leu | Thr | Thr | Ala | Leu | Arg | Asn | Ala | Ala | Ser | Leu | Ala |
| 10  |     |     |     |     | 15  |     |     |     |     | 20  |     |     |     |     | 25  |
| aac | gca | gct | gcc | gac | gcg | gct | cag | tct | gga | tca | gct | tca | aag | ttc | agc | 657 |
| Asn | Ala | Ala | Ala | Asp | Ala | Ala | Gln | Ser | Gly | Ser | Ala | Ser | Lys | Phe | Ser |
|     |     |     | 30  |     |     |     |     | 35  |     |     |     |     | 40  |     |     |
| gag | tac | ttc | aag | act | act | tct | agc | tct | acc | cgc | cag | acc | gtg | gct | gcg | 705 |
| Glu | Tyr | Phe | Lys | Thr | Thr | Ser | Ser | Ser | Thr | Arg | Gln | Thr | Val | Ala | Ala |
|     |     |     | 45  |     |     |     |     | 50  |     |     |     |     | 55  |     |     |
| cgt | ctt | cgg | gct | gtt | gcg | cgg | gag | gca | tct | tcg | tct | tct | tcg | gga | gcc | 753 |
| Arg | Leu | Arg | Ala | Val | Ala | Arg | Glu | Ala | Ser | Ser | Ser | Ser | Ser | Gly | Ala |
|     |     | 60  |     |     |     |     | 65  |     |     |     |     | 70  |     |     |     |
| acc | acg | tac | tac | tgc | gac | gat | ccc | tac | ggc | tac | tgt | tcc | tcc | aac | gtc | 801 |
| Thr | Thr | Tyr | Tyr | Cys | Asp | Asp | Pro | Tyr | Gly | Tyr | Cys | Ser | Ser | Asn | Val |
|     | 75  |     |     |     |     | 80  |     |     |     |     | 85  |     |     |     |     |
| ctg | gct | tac | acc | ctg | cct | tca | tac | aac | ata | atc | gcc | aac | tgt | gac | att | 849 |
| Leu | Ala | Tyr | Thr | Leu | Pro | Ser | Tyr | Asn | Ile | Ile | Ala | Asn | Cys | Asp | Ile |
| 90  |     |     |     |     | 95  |     |     |     |     | 100 |     |     |     |     | 105 |
| ttc | tat | act | tac | ctg | ccg | gct | ctg | acc | agt | acc | tgt | cac | gct | cag | gat | 897 |
| Phe | Tyr | Thr | Tyr | Leu | Pro | Ala | Leu | Thr | Ser | Thr | Cys | His | Ala | Gln | Asp |
|     |     |     |     | 110 |     |     |     |     | 115 |     |     |     |     | 120 |     |
| caa | gcg | acc | act | gcc | ctt | cac | gag | ttc | acc | cat | gcg | cct | ggc | gtc | tac | 945 |
| Gln | Ala | Thr | Thr | Ala | Leu | His | Glu | Phe | Thr | His | Ala | Pro | Gly | Val | Tyr |
|     |     |     | 125 |     |     |     |     | 130 |     |     |     |     | 135 |     |     |
| agc | cct | ggc | acg | gac | gac | ctg | gcg | tat | ggc | tac | cag | gct | gcg | atg | ggt | 993 |
| Ser | Pro | Gly | Thr | Asp | Asp | Leu | Ala | Tyr | Gly | Tyr | Gln | Ala | Ala | Met | Gly |
|     |     |     | 140 |     |     |     |     | 145 |     |     |     |     | 150 |     |     |
| ctc | agc | agc | agc | cag | gct | gtc | atg | aac | gct | gac | acc | tac | gct | ctc | tat | 1041 |
| Leu | Ser | Ser | Ser | Gln | Ala | Val | Met | Asn | Ala | Asp | Thr | Tyr | Ala | Leu | Tyr |
|     |     |     | 155 |     |     |     |     | 160 |     |     |     |     | 165 |     |     |
| gcg | aat | gcc | ata | tac | ctt | ggt | tgc | taa |     |     |     |     |     |     |     | 1068 |
| Ala | Asn | Ala | Ile | Tyr | Leu | Gly | Cys |     |     |     |     |     |     |     |     |
| 170 |     |     |     | 175 |     |     |     |     |     |     |     |     |     |     |     |

<210> SEQ ID NO 3
<211> LENGTH: 355
<212> TYPE: PRT
<213> ORGANISM: Thermoascus aurantiacus

<400> SEQUENCE: 3

Met Arg Leu Val  Ala Ser Leu Thr  Ala Leu Val Ala Leu Ser  Val
         -175              -170              -165

Pro Val Phe Pro  Ala Ala Val Asn  Val Lys Arg Ala Ser Ser  Tyr
         -160              -155              -150

```
Leu Glu Ile Thr  Leu Ser Gln Val  Ser Asn Thr Leu  Ile Lys Ala
         -145             -140             -135

Val Val Gln Asn  Thr Gly Ser Asp  Glu Leu Ser Phe  Val His Leu
         -130             -125             -120

Asn Phe Phe Lys  Asp Pro Ala Pro  Val Lys Lys Val  Ser Val Tyr
         -115             -110             -105

Arg Asp Gly Ser  Glu Val Gln Phe  Glu Gly Ile Leu  Ser Arg Tyr Lys
         -100              -95                       -90

Ser Thr Gly Leu  Ser Arg Asp Ala  Phe Thr Tyr Leu  Ala Pro Gly Glu
          -85              -80               -75

Ser Val Glu Asp  Val Phe Asp Ile  Ala Ser Thr Tyr  Asp Leu Thr Ser
          -70              -65               -60

Gly Gly Pro Val  Thr Ile Arg Thr  Glu Gly Val Val  Pro Tyr Ala Thr
-55               -50              -45                        -40

Ala Asn Ser Thr  Asp Ile Ala Gly  Tyr Ile Ser Tyr  Ser Ser Asn Val
          -35              -30                               -25

Leu Thr Ile Asp  Val Asp Gly Ala  Ala Ala Thr Val  Ser Lys Ala
          -20              -15                -10

Ile Thr Pro Leu  Asp Arg Arg Thr  Arg Ile Ser Ser  Cys Ser Gly Ser
           -5            -1   1                 5

Arg Gln Ser Ala  Leu Thr Thr Ala  Leu Arg Asn Ala  Ala Ser Leu Ala
10                        15                20                  25

Asn Ala Ala Asp  Ala Ala Gln Ser  Gly Ser Ala Ser  Lys Phe Ser
              30                        35                  40

Glu Tyr Phe Lys  Thr Thr Ser Ser  Ser Thr Arg Gln  Thr Val Ala Ala
             45                        50                   55

Arg Leu Arg Ala  Val Ala Arg Glu  Ala Ser Ser Ser  Ser Gly Ala
              60                        65                   70

Thr Thr Tyr Tyr  Cys Asp Asp Pro  Tyr Gly Tyr Cys  Ser Ser Asn Val
75                        80                85

Leu Ala Tyr Thr  Leu Pro Ser Tyr  Asn Ile Ile Ala  Asn Cys Asp Ile
90                        95                100                105

Phe Tyr Thr Tyr  Leu Pro Ala Leu  Thr Ser Thr Cys  His Ala Gln Asp
             110                       115                  120

Gln Ala Thr Thr  Ala Leu His Glu  Phe Thr His Ala  Pro Gly Val Tyr
             125                       130                  135

Ser Pro Gly Thr  Asp Asp Leu Ala  Tyr Gly Tyr Gln  Ala Ala Met Gly
             140                       145                  150

Leu Ser Ser Ser  Gln Ala Val Met  Asn Ala Asp Thr  Tyr Ala Leu Tyr
155                       160                165

Ala Asn Ala Ile  Tyr Leu Gly Cys
170                       175

<210> SEQ ID NO 4
<211> LENGTH: 49
<212> TYPE: DNA
<213> ORGANISM: Artificial Sequence
<220> FEATURE:
<223> OTHER INFORMATION: Synthetic Construct

<400> SEQUENCE: 4
aacgacggta cccgggggatc ggatccatgc ggctcgttgc ttccctaac          49

<210> SEQ ID NO 5
<211> LENGTH: 48
```

```
<212> TYPE: DNA
<213> ORGANISM: Artificial Sequence
<220> FEATURE:
<223> OTHER INFORMATION: Artificial Construct

<400> SEQUENCE: 5
ctaattacat gatgcggccc ttaattaatt agcaaccaag gtatatgg                          48

<210> SEQ ID NO 6
<211> LENGTH: 20
<212> TYPE: DNA
<213> ORGANISM: Artificial Sequence
<220> FEATURE:
<223> OTHER INFORMATION: Artificial Construct

<400> SEQUENCE: 6
taggagttta gtgaacttgc                                                        20

<210> SEQ ID NO 7
<211> LENGTH: 18
<212> TYPE: DNA
<213> ORGANISM: Artificial Sequence
<220> FEATURE:
<223> OTHER INFORMATION: Artificial Construct

<400> SEQUENCE: 7
ttcgagcgtc ccaaaacc                                                          18

<210> SEQ ID NO 8
<211> LENGTH: 1851
<212> TYPE: DNA
<213> ORGANISM: Penicillium oxalicum
<220> FEATURE:
<221> NAME/KEY: CDS
<222> LOCATION: (1)..(1848)
<220> FEATURE:
<221> NAME/KEY: misc_signal
<222> LOCATION: (1)..(63)
<223> OTHER INFORMATION: Signal predicted using Signal P (Nielsen et al,
      1997, Protein Engineering 10: 1-6)
<220> FEATURE:
<221> NAME/KEY: mat_peptide
<222> LOCATION: (64)..(1848)

<400> SEQUENCE: 8 atg cgt ctc act cta tta tca ggt gta gcc ggc gtt ctc tgc gca gga              48
Met Arg Leu Thr Leu Leu Ser Gly Val Ala Gly Val Leu Cys Ala Gly
    -20                 -15                 -10 cag ctg acg gcg gcg cgt cct gat ccc aag ggt ggg aat ctg acg ccg              96
Gln Leu Thr Ala Ala Arg Pro Asp Pro Lys Gly Gly Asn Leu Thr Pro
 -5              -1   1                   5                  10 ttc atc cac aaa gag ggc gag cgg tcg ctc caa ggc atc ttg gac aat             144
Phe Ile His Lys Glu Gly Glu Arg Ser Leu Gln Gly Ile Leu Asp Asn
             15                  20                  25 ctc ggt ggg cga ggt aag aaa aca ccc ggc act gcc gca ggg ttg ttt             192
Leu Gly Gly Arg Gly Lys Lys Thr Pro Gly Thr Ala Ala Gly Leu Phe
         30                  35                  40 att gcc agt cca aac aca gag aat cca aac tat tat tat aca tgg act             240
Ile Ala Ser Pro Asn Thr Glu Asn Pro Asn Tyr Tyr Tyr Thr Trp Thr
     45                  50                  55 cgt gac tca gct ttg act gcc aag tgc ttg atc gac ctg ttc gaa gac             288
Arg Asp Ser Ala Leu Thr Ala Lys Cys Leu Ile Asp Leu Phe Glu Asp
 60                  65                  70                  75 tct cgg gca aag ttt cca att gac cgc aaa tac ttg gaa aca gga att             336
Ser Arg Ala Lys Phe Pro Ile Asp Arg Lys Tyr Leu Glu Thr Gly Ile
                 80                  85                  90
```

-continued

| | |
|---|---|
| cgg gac tac gtg tcg tcc caa gca atc ctc cag agt gtg tct aat cct<br>Arg Asp Tyr Val Ser Ser Gln Ala Ile Leu Gln Ser Val Ser Asn Pro<br>              95                    100                 105 | 384 |
| tct gga acc ctg aag gat ggc tct ggt ctg ggt gaa ccc aag ttt gag<br>Ser Gly Thr Leu Lys Asp Gly Ser Gly Leu Gly Glu Pro Lys Phe Glu<br>     110                   115                   120 | 432 |
| att gac ctg aat ccc ttt tcg ggt gcc tgg ggt cgg cct cag cgg gat<br>Ile Asp Leu Asn Pro Phe Ser Gly Ala Trp Gly Arg Pro Gln Arg Asp<br>125                   130                   135 | 480 |
| ggc cca gcg ctg cga gcg acc gct atg atc acc tac gcc aac tac ctg<br>Gly Pro Ala Leu Arg Ala Thr Ala Met Ile Thr Tyr Ala Asn Tyr Leu<br>140                   145                   150                 155 | 528 |
| ata tcc cat ggt cag aaa tcg gat gtg tca cag gtc atg tgg ccg att<br>Ile Ser His Gly Gln Lys Ser Asp Val Ser Gln Val Met Trp Pro Ile<br>                  160                   165                170 | 576 |
| att gcc aat gat cta gca tat gtt ggt caa tac tgg aat aat acc gga<br>Ile Ala Asn Asp Leu Ala Tyr Val Gly Gln Tyr Trp Asn Asn Thr Gly<br>              175                   180                 185 | 624 |
| ttt gac ctg tgg gaa gag gtg gat ggg tca agc ttt ttc acg att gcg<br>Phe Asp Leu Trp Glu Glu Val Asp Gly Ser Ser Phe Phe Thr Ile Ala<br>     190                   195                   200 | 672 |
| gtc cag cac cga gcc ctt gtt gaa ggc tcg caa ctg gcg aaa aag ctc<br>Val Gln His Arg Ala Leu Val Glu Gly Ser Gln Leu Ala Lys Lys Leu<br>205                   210                   215 | 720 |
| ggc aag tcc tgc gat gcc tgt gat tct cag cct ccc cag ata ttg tgt<br>Gly Lys Ser Cys Asp Ala Cys Asp Ser Gln Pro Pro Gln Ile Leu Cys<br>220                   225                   230                235 | 768 |
| ttc ctg cag agt ttc tgg aac gga aag tac atc acc tcc aac atc aac<br>Phe Leu Gln Ser Phe Trp Asn Gly Lys Tyr Ile Thr Ser Asn Ile Asn<br>              240                   245                 250 | 816 |
| acg caa gca agc cgc tct ggt atc gac ctg gac tct gtc ctg gga agc<br>Thr Gln Ala Ser Arg Ser Gly Ile Asp Leu Asp Ser Val Leu Gly Ser<br>                 255                   260                265 | 864 |
| att cat acc ttt gat ccc gaa gca gcc tgt gac gat gca act ttc cag<br>Ile His Thr Phe Asp Pro Glu Ala Ala Cys Asp Asp Ala Thr Phe Gln<br>             270                   275                 280 | 912 |
| cct tgt tct gcc cgc gct ctg gcg aac cac aag gtc tat gtg gat tcc<br>Pro Cys Ser Ala Arg Ala Leu Ala Asn His Lys Val Tyr Val Asp Ser<br>285                   290                   295 | 960 |
| ttc cgc tct atc tac aag att aat gcg ggt ctt gca gag gga tcg gct<br>Phe Arg Ser Ile Tyr Lys Ile Asn Ala Gly Leu Ala Glu Gly Ser Ala<br>300                   305                   310                315 | 1008 |
| gcc aac gtt ggc cgc tac ccc gag gat gtt tac caa gga ggc aat cca<br>Ala Asn Val Gly Arg Tyr Pro Glu Asp Val Tyr Gln Gly Gly Asn Pro<br>              320                   325                 330 | 1056 |
| tgg tat ctc gcc acc cta ggc gca tct gaa ttg ctt tac gac gcc ttg<br>Trp Tyr Leu Ala Thr Leu Gly Ala Ser Glu Leu Leu Tyr Asp Ala Leu<br>             335                   340                345 | 1104 |
| tac cag tgg gac aga ctt ggc aaa ctt gaa gtc tcg gag acc tcg ttg<br>Tyr Gln Trp Asp Arg Leu Gly Lys Leu Glu Val Ser Glu Thr Ser Leu<br>350                   355                   360 | 1152 |
| tca ttc ttc aaa gac ttt gac gcg acc gtg aaa att ggc tcg tac tcg<br>Ser Phe Phe Lys Asp Phe Asp Ala Thr Val Lys Ile Gly Ser Tyr Ser<br>365                   370                   375 | 1200 |
| agg aac agc aag acc tac aag aaa ttg acc cag tcc atc aag tcg tac<br>Arg Asn Ser Lys Thr Tyr Lys Lys Leu Thr Gln Ser Ile Lys Ser Tyr<br>380                   385                   390                395 | 1248 |
| gcg gac ggg ttc atc cag tta gtg cag cag tac act cct tct aat gga<br>Ala Asp Gly Phe Ile Gln Leu Val Gln Gln Tyr Thr Pro Ser Asn Gly | 1296 |

```
                        400                 405                 410
tct ctg gcc gag caa tac gat cgc aat acg gct gct cct ctc tct gca       1344
Ser Leu Ala Glu Gln Tyr Asp Arg Asn Thr Ala Ala Pro Leu Ser Ala
            415                 420                 425 aac gat ctg act tgg tca ttt gcc tct ttc ttg acg gct acg caa cgc       1392
Asn Asp Leu Thr Trp Ser Phe Ala Ser Phe Leu Thr Ala Thr Gln Arg
                430                 435                 440 cgc gat gcc gtg gtt cct ccc tcc tgg ggc gca aag tcg gca aac aaa       1440
Arg Asp Ala Val Val Pro Pro Ser Trp Gly Ala Lys Ser Ala Asn Lys
            445                 450                 455 gtc cca acc act tgt tca gcc tcc cct gtt gtg ggt act tat aag gcg       1488
Val Pro Thr Thr Cys Ser Ala Ser Pro Val Val Gly Thr Tyr Lys Ala
460                 465                 470                 475 ccc acg gca act ttc tca tcc aag act aag tgc gtc ccc gct aaa gat       1536
Pro Thr Ala Thr Phe Ser Ser Lys Thr Lys Cys Val Pro Ala Lys Asp
                480                 485                 490 att gtg cct atc acg ttc tac ctg att gag aac act tac tat gga gag       1584
Ile Val Pro Ile Thr Phe Tyr Leu Ile Glu Asn Thr Tyr Tyr Gly Glu
            495                 500                 505 aac gtc ttc atg agt ggc aac att act gcg ctg ggt aac tgg gac gcc       1632
Asn Val Phe Met Ser Gly Asn Ile Thr Ala Leu Gly Asn Trp Asp Ala
                510                 515                 520 aag aaa ggc ttc cca ctc acc gca aac ctc tac acg caa gat caa aac       1680
Lys Lys Gly Phe Pro Leu Thr Ala Asn Leu Tyr Thr Gln Asp Gln Asn
            525                 530                 535 ttg tgg ttc gcc agt gtc gag ttc atc cca gca ggc aca ccc ttt gag       1728
Leu Trp Phe Ala Ser Val Glu Phe Ile Pro Ala Gly Thr Pro Phe Glu
540                 545                 550                 555 tac aag tac tac aag gtc gag ccc aat ggc gat att act tgg gag aag       1776
Tyr Lys Tyr Tyr Lys Val Glu Pro Asn Gly Asp Ile Thr Trp Glu Lys
                560                 565                 570 ggt ccc aac cgg gtg ttc gtc gct ccc acg gga tgc cca gtt cag cct       1824
Gly Pro Asn Arg Val Phe Val Ala Pro Thr Gly Cys Pro Val Gln Pro
            575                 580                 585 cac tcc aac gac gtg tgg cag ttt tga                                   1851
His Ser Asn Asp Val Trp Gln Phe
            590                 595

<210> SEQ ID NO 9
<211> LENGTH: 616
<212> TYPE: PRT
<213> ORGANISM: Penicillium oxalicum

<400> SEQUENCE: 9

Met Arg Leu Thr Leu Leu Ser Gly Val Ala Gly Val Leu Cys Ala Gly
    -20                 -15                 -10

Gln Leu Thr Ala Ala Arg Pro Asp Pro Lys Gly Gly Asn Leu Thr Pro
 -5                  -1   1               5                  10

Phe Ile His Lys Glu Gly Glu Arg Ser Leu Gln Gly Ile Leu Asp Asn
                 15                 20                  25

Leu Gly Gly Arg Gly Lys Lys Thr Pro Gly Thr Ala Ala Gly Leu Phe
             30                  35                  40

Ile Ala Ser Pro Asn Thr Glu Asn Pro Asn Tyr Tyr Tyr Thr Trp Thr
         45                  50                  55

Arg Asp Ser Ala Leu Thr Ala Lys Cys Leu Ile Asp Leu Phe Glu Asp
 60                  65                  70                  75

Ser Arg Ala Lys Phe Pro Ile Asp Arg Lys Tyr Leu Glu Thr Gly Ile
                 80                  85                  90
```

-continued

```
Arg Asp Tyr Val Ser Ser Gln Ala Ile Leu Gln Ser Val Ser Asn Pro
             95                 100                 105

Ser Gly Thr Leu Lys Asp Gly Ser Gly Leu Gly Glu Pro Lys Phe Glu
         110                 115                 120

Ile Asp Leu Asn Pro Phe Ser Gly Ala Trp Gly Arg Pro Gln Arg Asp
     125                 130                 135

Gly Pro Ala Leu Arg Ala Thr Ala Met Ile Thr Tyr Ala Asn Tyr Leu
140                 145                 150                 155

Ile Ser His Gly Gln Lys Ser Asp Val Ser Gln Val Met Trp Pro Ile
                 160                 165                 170

Ile Ala Asn Asp Leu Ala Tyr Val Gly Gln Tyr Trp Asn Asn Thr Gly
             175                 180                 185

Phe Asp Leu Trp Glu Val Asp Gly Ser Ser Phe Phe Thr Ile Ala
         190                 195                 200

Val Gln His Arg Ala Leu Val Glu Gly Ser Gln Leu Ala Lys Lys Leu
     205                 210                 215

Gly Lys Ser Cys Asp Ala Cys Asp Ser Gln Pro Gln Ile Leu Cys
220                 225                 230                 235

Phe Leu Gln Ser Phe Trp Asn Gly Lys Tyr Ile Thr Ser Asn Ile Asn
                 240                 245                 250

Thr Gln Ala Ser Arg Ser Gly Ile Asp Leu Asp Ser Val Leu Gly Ser
             255                 260                 265

Ile His Thr Phe Asp Pro Glu Ala Ala Cys Asp Ala Thr Phe Gln
         270                 275                 280

Pro Cys Ser Ala Arg Ala Leu Ala Asn His Lys Val Tyr Val Asp Ser
285                 290                 295

Phe Arg Ser Ile Tyr Lys Ile Asn Ala Gly Leu Ala Glu Gly Ser Ala
300                 305                 310                 315

Ala Asn Val Gly Arg Tyr Pro Glu Asp Val Tyr Gln Gly Gly Asn Pro
             320                 325                 330

Trp Tyr Leu Ala Thr Leu Gly Ala Ser Glu Leu Leu Tyr Asp Ala Leu
         335                 340                 345

Tyr Gln Trp Asp Arg Leu Gly Lys Leu Glu Val Ser Glu Thr Ser Leu
     350                 355                 360

Ser Phe Phe Lys Asp Phe Asp Ala Thr Val Lys Ile Gly Ser Tyr Ser
365                 370                 375

Arg Asn Ser Lys Thr Tyr Lys Lys Leu Thr Gln Ser Ile Lys Ser Tyr
380                 385                 390                 395

Ala Asp Gly Phe Ile Gln Leu Val Gln Gln Tyr Thr Pro Ser Asn Gly
             400                 405                 410

Ser Leu Ala Glu Gln Tyr Asp Arg Asn Thr Ala Ala Pro Leu Ser Ala
         415                 420                 425

Asn Asp Leu Thr Trp Ser Phe Ala Ser Phe Leu Thr Ala Thr Gln Arg
     430                 435                 440

Arg Asp Ala Val Val Pro Pro Ser Trp Gly Ala Lys Ser Ala Asn Lys
445                 450                 455

Val Pro Thr Thr Cys Ser Ala Ser Pro Val Val Gly Thr Tyr Lys Ala
460                 465                 470                 475

Pro Thr Ala Thr Phe Ser Ser Lys Thr Lys Cys Val Pro Ala Lys Asp
             480                 485                 490

Ile Val Pro Ile Thr Phe Tyr Leu Ile Glu Asn Thr Tyr Tyr Gly Glu
         495                 500                 505

Asn Val Phe Met Ser Gly Asn Ile Thr Ala Leu Gly Asn Trp Asp Ala
```

```
                510             515             520
Lys Lys Gly Phe Pro Leu Thr Ala Asn Leu Tyr Thr Gln Asp Gln Asn
525             530             535

Leu Trp Phe Ala Ser Val Glu Phe Ile Pro Ala Gly Thr Pro Phe Glu
540             545             550             555

Tyr Lys Tyr Tyr Lys Val Glu Pro Asn Gly Asp Ile Thr Trp Glu Lys
                560             565             570

Gly Pro Asn Arg Val Phe Val Ala Pro Thr Gly Cys Pro Val Gln Pro
            575             580             585

His Ser Asn Asp Val Trp Gln Phe
            590             595

<210> SEQ ID NO 10
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10 atg agg cgg gtg gtt gcc ctc ttc att gca att ttg atg ctt gga agc     48
Met Arg Arg Val Val Ala Leu Phe Ile Ala Ile Leu Met Leu Gly Ser
        -25             -20             -15 atc gtt gga gcg aac gtt aag agc gtt ggc gcg gcg gag ccg aag ccg     96
Ile Val Gly Ala Asn Val Lys Ser Val Gly Ala Ala Glu Pro Lys Pro
    -10             -5             -1 1               5 ctc aac gtc ata ata gtc tgg cac cag cac cag ccc tac tac tac gac    144
Leu Asn Val Ile Ile Val Trp His Gln His Gln Pro Tyr Tyr Tyr Asp
            10              15              20 cct gtc cag gac gtc tac acc agg ccc tgg gtc agg ctc cac gcg gcg    192
Pro Val Gln Asp Val Tyr Thr Arg Pro Trp Val Arg Leu His Ala Ala
        25              30              35 aac aac tac tgg aag atg gcc cac tac ctg agc cag tac ccg gag gtt    240
Asn Asn Tyr Trp Lys Met Ala His Tyr Leu Ser Gln Tyr Pro Glu Val
    40              45              50 cac gcc acc att gac ctc tcg ggt tcg ctg ata gcc cag ctt gcc gac    288
His Ala Thr Ile Asp Leu Ser Gly Ser Leu Ile Ala Gln Leu Ala Asp
55              60              65 tac atg aac ggc aag aag gac acc tac cag ata atc acc gag aag ata    336
Tyr Met Asn Gly Lys Lys Asp Thr Tyr Gln Ile Ile Thr Glu Lys Ile
70              75              80              85 gcc aac ggg gaa ccc ctc acc gtc gac gag aag tgg ttc atg ctc cag    384
Ala Asn Gly Glu Pro Leu Thr Val Asp Glu Lys Trp Phe Met Leu Gln
        90              95             100 gca ccg gga ggg ttc ttc gac aac acc atc ccc tgg aac ggt gaa ccg    432
Ala Pro Gly Gly Phe Phe Asp Asn Thr Ile Pro Trp Asn Gly Glu Pro
    105             110             115 ata acc gac ccc aac ggc aac ccg ata agg gac ttc tgg gac cgc tac    480
Ile Thr Asp Pro Asn Gly Asn Pro Ile Arg Asp Phe Trp Asp Arg Tyr
120             125             130 acg gag ctg aag aac aag atg ctc agc gca aag gcc aag tac gca aac    528
Thr Glu Leu Lys Asn Lys Met Leu Ser Ala Lys Ala Lys Tyr Ala Asn
135             140             145 ttc gtg act gag agc cag aag gtc gct gtg acg aac gag ttc aca gag    576
```

```
                Phe Val Thr Glu Ser Gln Lys Val Ala Val Thr Asn Glu Phe Thr Glu
                150                 155                 160                 165 cag gac tac ata gac cta gcg gtt ctc ttc aat ctc gct tgg att gac              624
Gln Asp Tyr Ile Asp Leu Ala Val Leu Phe Asn Leu Ala Trp Ile Asp
                170                 175                 180 tac aat tac atc acg agc acg ccg gag ttc aag gcc ctc tac gac aag              672
Tyr Asn Tyr Ile Thr Ser Thr Pro Glu Phe Lys Ala Leu Tyr Asp Lys
                185                 190                 195 gtt gac gag ggc ggc tat aca agg gcg gac gtc aaa acc gtt ctc gac              720
Val Asp Glu Gly Gly Tyr Thr Arg Ala Asp Val Lys Thr Val Leu Asp
                200                 205                 210 gcc cag atc tgg ctt ctc aac cac acc ttc gag gag cac gag aag ata              768
Ala Gln Ile Trp Leu Leu Asn His Thr Phe Glu Glu His Glu Lys Ile
                215                 220                 225 aac ctc ctc ctc gga aac ggc aac gtc gag gtc acg gtc gtt ccc tac              816
Asn Leu Leu Leu Gly Asn Gly Asn Val Glu Val Thr Val Val Pro Tyr
230                 235                 240                 245 gcc cac ccg ata ggc ccg ata ctc aac gac ttc ggc tgg gac agc gac              864
Ala His Pro Ile Gly Pro Ile Leu Asn Asp Phe Gly Trp Asp Ser Asp
                250                 255                 260 ttc aac gac cag gtc aag aag gcc gac gaa ctg tac aag ccg tac ctc              912
Phe Asn Asp Gln Val Lys Lys Ala Asp Glu Leu Tyr Lys Pro Tyr Leu
                265                 270                 275 ggc ggc ggc acc gcg gtt cca aaa ggc gga tgg gcg gct gag agc gcc              960
Gly Gly Gly Thr Ala Val Pro Lys Gly Gly Trp Ala Ala Glu Ser Ala
                280                 285                 290 ctc aac gac aaa act ctg gag atc ctc gcc gag aac ggc tgg gag tgg             1008
Leu Asn Asp Lys Thr Leu Glu Ile Leu Ala Glu Asn Gly Trp Glu Trp
295                 300                 305 gtc atg acc gac cag atg gtt ctc gga aag ctc ggc att gag gga acc             1056
Val Met Thr Asp Gln Met Val Leu Gly Lys Leu Gly Ile Glu Gly Thr
310                 315                 320                 325 gtc gag aac tac cac aag ccc tgg gtg gcc gag ttc aac gga aag aag             1104
Val Glu Asn Tyr His Lys Pro Trp Val Ala Glu Phe Asn Gly Lys Lys
                330                 335                 340 ata tac ctc ttc cca aga aat cac gat cta agt gac aga gtt ggc ttt             1152
Ile Tyr Leu Phe Pro Arg Asn His Asp Leu Ser Asp Arg Val Gly Phe
                345                 350                 355 acc tac agc gga atg aac cag cag cag gcc gtt gag gac ttc gtc aac             1200
Thr Tyr Ser Gly Met Asn Gln Gln Gln Ala Val Glu Asp Phe Val Asn
                360                 365                 370 gag ctc ctc aag ctc cag aag cag aac tac gat ggc tcg ctg gtt tac             1248
Glu Leu Leu Lys Leu Gln Lys Gln Asn Tyr Asp Gly Ser Leu Val Tyr
                375                 380                 385 gtg gtc acg ctc gac ggc gag aac ccc gtg gag aac tac ccc tac gac             1296
Val Val Thr Leu Asp Gly Glu Asn Pro Val Glu Asn Tyr Pro Tyr Asp
390                 395                 400                 405 ggg gag ctc ttc ctc acc gaa ctc tac aag aag ctg acc gaa ctc cag             1344
Gly Glu Leu Phe Leu Thr Glu Leu Tyr Lys Lys Leu Thr Glu Leu Gln
                410                 415                 420 gag cag ggt ctc ata aga acc ctc acc ccg agc gag tac atc cag ctc             1392
Glu Gln Gly Leu Ile Arg Thr Leu Thr Pro Ser Glu Tyr Ile Gln Leu
                425                 430                 435 tac ggc gac aag gcc aac aag ctc aca cct cgg atg atg gag cgc ctt             1440
Tyr Gly Asp Lys Ala Asn Lys Leu Thr Pro Arg Met Met Glu Arg Leu
                440                 445                 450 gac ctc acc gga gac aac gtt aac gcc ctc ctc aag gcc cag agc ctc             1488
Asp Leu Thr Gly Asp Asn Val Asn Ala Leu Leu Lys Ala Gln Ser Leu
455                 460                 465
```

```
ggc gaa ctc tac gac atg acc ggc gtt aag gag gag atg cag tgg ccc    1536
Gly Glu Leu Tyr Asp Met Thr Gly Val Lys Glu Glu Met Gln Trp Pro
470                 475                 480                 485 gag agc agc tgg ata gac gga acc ctc tcc acg tgg ata ggc gag ccc    1584
Glu Ser Ser Trp Ile Asp Gly Thr Leu Ser Thr Trp Ile Gly Glu Pro
                490                 495                 500 cag gag aac tac ggc tgg tac tgg ctc tac atg gcc agg aag gcc ctt    1632
Gln Glu Asn Tyr Gly Trp Tyr Trp Leu Tyr Met Ala Arg Lys Ala Leu
            505                 510                 515 atg gag aac aag gat aaa atg agc cag gcg gac tgg gag aag gcc tac    1680
Met Glu Asn Lys Asp Lys Met Ser Gln Ala Asp Trp Glu Lys Ala Tyr
        520                 525                 530 gag tac ctg ctc cgc gcc gag gca agc gac tgg ttc tgg tgg tac gga    1728
Glu Tyr Leu Leu Arg Ala Glu Ala Ser Asp Trp Phe Trp Trp Tyr Gly
    535                 540                 545 agc gac cag gac agc ggc cag gac tac acc ttc gac cgc tac ctg aag    1776
Ser Asp Gln Asp Ser Gly Gln Asp Tyr Thr Phe Asp Arg Tyr Leu Lys
550                 555                 560                 565 acc tac ctc tac gag atg tac aag ctg gca gga gtc gag ccg ccg agc    1824
Thr Tyr Leu Tyr Glu Met Tyr Lys Leu Ala Gly Val Glu Pro Pro Ser
                570                 575                 580 tac ctc ttc ggc aac tac ttc ccg gac gga gag ccc tac acc acg agg    1872
Tyr Leu Phe Gly Asn Tyr Phe Pro Asp Gly Glu Pro Tyr Thr Thr Arg
            585                 590                 595 ggc ctg gtc gga ctc aag gac ggc gag atg aag aac ttc tcc agc atg    1920
Gly Leu Val Gly Leu Lys Asp Gly Glu Met Lys Asn Phe Ser Ser Met
        600                 605                 610 tcc ccg ctg gca aag ggc gtg agc gtc tat ttc gac ggc gag ggg ata    1968
Ser Pro Leu Ala Lys Gly Val Ser Val Tyr Phe Asp Gly Glu Gly Ile
    615                 620                 625 cac ttc ata gtg aaa ggg aac ctg gac agg ttc gag gtg agc atc tgg    2016
His Phe Ile Val Lys Gly Asn Leu Asp Arg Phe Glu Val Ser Ile Trp
630                 635                 640                 645 gag aag gat gag cgc gtt ggc aac acg ttc acc cgc ctc caa gag aag    2064
Glu Lys Asp Glu Arg Val Gly Asn Thr Phe Thr Arg Leu Gln Glu Lys
                650                 655                 660 ccg gac gag ttg agc tat ttc atg ttc cca ttc tca agg gac agc gtt    2112
Pro Asp Glu Leu Ser Tyr Phe Met Phe Pro Phe Ser Arg Asp Ser Val
            665                 670                 675 ggt ctc ctc ata acc aag cac gtc gtg tac gag aac gga aag gcc gag    2160
Gly Leu Leu Ile Thr Lys His Val Val Tyr Glu Asn Gly Lys Ala Glu
        680                 685                 690 ata tac ggc gcc acc gac tac gag aag agc gag aag ctt ggg gaa gcc    2208
Ile Tyr Gly Ala Thr Asp Tyr Glu Lys Ser Glu Lys Leu Gly Glu Ala
    695                 700                 705 acc gtc aag aac acg agc gaa gga atc gaa gtc gtc ctt ccc ttt gac    2256
Thr Val Lys Asn Thr Ser Glu Gly Ile Glu Val Val Leu Pro Phe Asp
710                 715                 720                 725 tac ata gaa aac ccc tcc gac ttc tac ttc gct gtc tcg acg gtc aaa    2304
Tyr Ile Glu Asn Pro Ser Asp Phe Tyr Phe Ala Val Ser Thr Val Lys
                730                 735                 740 gat gga gac ctt gag gtg ata agc act cct gtg gag ctc aag ctc ccg    2352
Asp Gly Asp Leu Glu Val Ile Ser Thr Pro Val Glu Leu Lys Leu Pro
            745                 750                 755 acc gag gtc aag gga gtc gtc ata gcc gat ata acc gac cca gaa ggc    2400
Thr Glu Val Lys Gly Val Val Ile Ala Asp Ile Thr Asp Pro Glu Gly
        760                 765                 770 gac gac cat ggg ccc gga aac tac act tat ccc acg gac aag gtc ttc    2448
Asp Asp His Gly Pro Gly Asn Tyr Thr Tyr Pro Thr Asp Lys Val Phe
    775                 780                 785
```

```
aag cca ggt gtt ttc gac ctc ctc cgc ttc agg atg ctc gaa cag acg       2496
Lys Pro Gly Val Phe Asp Leu Leu Arg Phe Arg Met Leu Glu Gln Thr
790                 795                 800                 805 gag agc tac gtc atg gag ttc tac ttc aag gac cta ggt ggt aac ccg       2544
Glu Ser Tyr Val Met Glu Phe Tyr Phe Lys Asp Leu Gly Gly Asn Pro
                810                 815                 820 tgg aac gga ccc aac ggc ttc agc ctc cag ata atc gag gtc tac ctc       2592
Trp Asn Gly Pro Asn Gly Phe Ser Leu Gln Ile Ile Glu Val Tyr Leu
            825                 830                 835 gac ttc aag gac ggt gga aac agt tcg gcc att aag atg ttc ccc gac       2640
Asp Phe Lys Asp Gly Gly Asn Ser Ser Ala Ile Lys Met Phe Pro Asp
840                 845                 850 gga ccg gga gcc aac gtc aac ctc gac ccc gag cat cca tgg gac gtt       2688
Gly Pro Gly Ala Asn Val Asn Leu Asp Pro Glu His Pro Trp Asp Val
                855                 860                 865 gcc ttc agg ata gcg ggc tgg gac tac gga aac ctc atc atc ctg ccg       2736
Ala Phe Arg Ile Ala Gly Trp Asp Tyr Gly Asn Leu Ile Ile Leu Pro
870                 875                 880                 885 aac gga acg gcc atc cag ggc gag atg cag att tcc gca gat ccg gtt       2784
Asn Gly Thr Ala Ile Gln Gly Glu Met Gln Ile Ser Ala Asp Pro Val
                890                 895                 900 aag aac gcc ata ata gtc aag gtt cca aag aag tac atc gcc ata aac       2832
Lys Asn Ala Ile Ile Val Lys Val Pro Lys Lys Tyr Ile Ala Ile Asn
            905                 910                 915 gag gac tac ggc ctc tgg gga gac gtc ctc gtc ggc tcg cag gac ggc       2880
Glu Asp Tyr Gly Leu Trp Gly Asp Val Leu Val Gly Ser Gln Asp Gly
            920                 925                 930 tac ggc ccg gac aag tgg aga acg gcg gca gtg gat gcg gag cag tgg       2928
Tyr Gly Pro Asp Lys Trp Arg Thr Ala Ala Val Asp Ala Glu Gln Trp
            935                 940                 945 aag ctt gga ggt gcg gac ccg cag gca gtc ata aac ggc gtg gcc ccg       2976
Lys Leu Gly Gly Ala Asp Pro Gln Ala Val Ile Asn Gly Val Ala Pro
950                 955                 960                 965 cgc gtc att gat gag ctg gtt ccg cag ggc ttt gaa ccg acc cag gag       3024
Arg Val Ile Asp Glu Leu Val Pro Gln Gly Phe Glu Pro Thr Gln Glu
                970                 975                 980 gag cag ctg agc agc tac gat gca aac gac atg aag ctc gcc act gtc       3072
Glu Gln Leu Ser Ser Tyr Asp Ala Asn Asp Met Lys Leu Ala Thr Val
            985                 990                 995 aag gcg ctg cta ctc ctc aag cag ggc atc gtt gtg acc gac ccg           3117
Lys Ala Leu Leu Leu Leu Lys Gln Gly Ile Val Val Thr Asp Pro
                1000                1005                1010 gag gga gac gac cac ggg ccg gga acg tac acc tat ccg acg gac           3162
Glu Gly Asp Asp His Gly Pro Gly Thr Tyr Thr Tyr Pro Thr Asp
            1015                1020                1025 aaa gtt ttc aag ccc ggt gtt ttc gac ctc ctc aag ttc aag gtg           3207
Lys Val Phe Lys Pro Gly Val Phe Asp Leu Leu Lys Phe Lys Val
            1030                1035                1040 acc gag gga agc gac gac tgg acg ctg gag ttc cac ttc aaa gac           3252
Thr Glu Gly Ser Asp Asp Trp Thr Leu Glu Phe His Phe Lys Asp
            1045                1050                1055 ctc ggt gga aac ccg tgg aac ggg ccg aac ggc ttc agc ctg cag           3297
Leu Gly Gly Asn Pro Trp Asn Gly Pro Asn Gly Phe Ser Leu Gln
            1060                1065                1070 ata atc gag gta tac ttc gac ttc aag gag ggc ggg aac gtc tcg           3342
Ile Ile Glu Val Tyr Phe Asp Phe Lys Glu Gly Gly Asn Val Ser
            1075                1080                1085 gcc att aag atg ttc ccg gat ggg ccc gga agc aac gtc cgt ctt           3387
Ala Ile Lys Met Phe Pro Asp Gly Pro Gly Ser Asn Val Arg Leu
```

-continued

```
                            1090                     1095                     1100
        gat cca aat cac cca tgg gac ctg gcg ctt agg ata gcc ggc tgg          3432
        Asp Pro Asn His Pro Trp Asp Leu Ala Leu Arg Ile Ala Gly Trp
                            1105                     1110                     1115 gac tac gga aac ctg ata att ctg ccc gac gga acc gcc tac caa          3477
        Asp Tyr Gly Asn Leu Ile Ile Leu Pro Asp Gly Thr Ala Tyr Gln
                            1120                     1125                     1130 ggc gag atg cag att tcc gca gat ccg gtt aag aac gcc ata ata          3522
        Gly Glu Met Gln Ile Ser Ala Asp Pro Val Lys Asn Ala Ile Ile
                            1135                     1140                     1145 gtc aag gtt cca aag aag tac ctg aac ata tcc gac tac gga ctc          3567
        Val Lys Val Pro Lys Lys Tyr Leu Asn Ile Ser Asp Tyr Gly Leu
                            1150                     1155                     1160 tac acc gcc gtc atc gtg ggt tcc caa gac ggg tac ggc ccg gac          3612
        Tyr Thr Ala Val Ile Val Gly Ser Gln Asp Gly Tyr Gly Pro Asp
                            1165                     1170                     1175 aag tgg agg ccc gtg gcc gct gag gcc gag cag tgg aag ctc gga          3657
        Lys Trp Arg Pro Val Ala Ala Glu Ala Glu Gln Trp Lys Leu Gly
                            1180                     1185                     1190 ggc gca gac ccc cag gcg gtc ata gac aac ctc gta cca agg gtc          3702
        Gly Ala Asp Pro Gln Ala Val Ile Asp Asn Leu Val Pro Arg Val
                            1195                     1200                     1205 gtt gat gaa ctc gtg ccg gag ggc ttc aag cca acg cag gag gag          3747
        Val Asp Glu Leu Val Pro Glu Gly Phe Lys Pro Thr Gln Glu Glu
                            1210                     1215                     1220 cag ctg agc agc tac gac ctt gag aag aag acc ctg gcg acg gtg          3792
        Gln Leu Ser Ser Tyr Asp Leu Glu Lys Lys Thr Leu Ala Thr Val
                            1225                     1230                     1235 ctc atg gta ccg ctc gtc aat ggg act ggc ggc gag gaa cca acg          3837
        Leu Met Val Pro Leu Val Asn Gly Thr Gly Gly Glu Glu Pro Thr
                            1240                     1245                     1250 ccg acg gag agc cca acg gaa acg acg aca acc aca ccc agc gaa          3882
        Pro Thr Glu Ser Pro Thr Glu Thr Thr Thr Thr Thr Pro Ser Glu
                            1255                     1260                     1265 aca acc acc aca act tca acg acc acc ggc cca agc tca acg acc          3927
        Thr Thr Thr Thr Thr Ser Thr Thr Thr Gly Pro Ser Ser Thr Thr
                            1270                     1275                     1280 acc agc aca ccc ggc gga gga atc tgc ggc cca ggc att ata gcg          3972
        Thr Ser Thr Pro Gly Gly Gly Ile Cys Gly Pro Gly Ile Ile Ala
                            1285                     1290                     1295 ggc ctg gcc ctg ata ccg ctc ctc ctc aag agg agg aac tga              4014
        Gly Leu Ala Leu Ile Pro Leu Leu Leu Lys Arg Arg Asn
                            1300                     1305                     1310
```

<210> SEQ ID NO 11
<211> LENGTH: 1337
<212> TYPE: PRT
<213> ORGANISM: Thermococcus hydrothermalis

<400> SEQUENCE: 11

```
Met Arg Arg Val Val Ala Leu Phe Ile Ala Ile Leu Met Leu Gly Ser
              -25                  -20                  -15

Ile Val Gly Ala Asn Val Lys Ser Val Gly Ala Ala Glu Pro Lys Pro
        -10                   -5          -1   1                    5

Leu Asn Val Ile Ile Val Trp His Gln His Gln Pro Tyr Tyr Tyr Asp
                         10                   15                   20

Pro Val Gln Asp Val Tyr Thr Arg Pro Trp Val Arg Leu His Ala Ala
                 25                   30                   35

Asn Asn Tyr Trp Lys Met Ala His Tyr Leu Ser Gln Tyr Pro Glu Val
```

40                  45                  50
His Ala Thr Ile Asp Leu Ser Gly Ser Leu Ile Ala Gln Leu Ala Asp
        55                  60                  65

Tyr Met Asn Gly Lys Lys Asp Thr Tyr Gln Ile Ile Thr Glu Lys Ile
 70              75                  80                  85

Ala Asn Gly Glu Pro Leu Thr Val Asp Glu Lys Trp Phe Met Leu Gln
                    90                  95                 100

Ala Pro Gly Gly Phe Phe Asp Asn Thr Ile Pro Trp Asn Gly Glu Pro
                105                 110                 115

Ile Thr Asp Pro Asn Gly Asn Pro Ile Arg Asp Phe Trp Asp Arg Tyr
            120                 125                 130

Thr Glu Leu Lys Asn Lys Met Leu Ser Ala Lys Ala Lys Tyr Ala Asn
        135                 140                 145

Phe Val Thr Glu Ser Gln Lys Val Ala Val Thr Asn Glu Phe Thr Glu
150                 155                 160                 165

Gln Asp Tyr Ile Asp Leu Ala Val Leu Phe Asn Leu Ala Trp Ile Asp
                170                 175                 180

Tyr Asn Tyr Ile Thr Ser Thr Pro Glu Phe Lys Ala Leu Tyr Asp Lys
                185                 190                 195

Val Asp Glu Gly Gly Tyr Thr Arg Ala Asp Val Lys Thr Val Leu Asp
            200                 205                 210

Ala Gln Ile Trp Leu Leu Asn His Thr Phe Glu Glu His Glu Lys Ile
        215                 220                 225

Asn Leu Leu Leu Gly Asn Gly Asn Val Glu Val Thr Val Val Pro Tyr
230                 235                 240                 245

Ala His Pro Ile Gly Pro Ile Leu Asn Asp Phe Gly Trp Asp Ser Asp
                250                 255                 260

Phe Asn Asp Gln Val Lys Lys Ala Asp Glu Leu Tyr Lys Pro Tyr Leu
                265                 270                 275

Gly Gly Gly Thr Ala Val Pro Lys Gly Gly Trp Ala Ala Glu Ser Ala
            280                 285                 290

Leu Asn Asp Lys Thr Leu Glu Ile Leu Ala Glu Asn Gly Trp Glu Trp
        295                 300                 305

Val Met Thr Asp Gln Met Val Leu Gly Lys Leu Gly Ile Glu Gly Thr
310                 315                 320                 325

Val Glu Asn Tyr His Lys Pro Trp Val Ala Glu Phe Asn Gly Lys Lys
                330                 335                 340

Ile Tyr Leu Phe Pro Arg Asn His Asp Leu Ser Asp Arg Val Gly Phe
            345                 350                 355

Thr Tyr Ser Gly Met Asn Gln Gln Ala Val Glu Asp Phe Val Asn
        360                 365                 370

Glu Leu Leu Lys Leu Gln Lys Gln Asn Tyr Asp Gly Ser Leu Val Tyr
        375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
                410                 415                 420

Glu Gln Gly Leu Ile Arg Thr Leu Thr Pro Ser Glu Tyr Ile Gln Leu
            425                 430                 435

Tyr Gly Asp Lys Ala Asn Lys Leu Thr Pro Arg Met Met Glu Arg Leu
        440                 445                 450

Asp Leu Thr Gly Asp Asn Val Asn Ala Leu Leu Lys Ala Gln Ser Leu
        455                 460                 465

-continued

```
Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
            490                 495                 500

Gln Glu Asn Tyr Gly Trp Tyr Trp Leu Tyr Met Ala Arg Lys Ala Leu
                505                 510                 515

Met Glu Asn Lys Asp Lys Met Ser Gln Ala Asp Trp Glu Lys Ala Tyr
            520                 525                 530

Glu Tyr Leu Leu Arg Ala Glu Ala Ser Asp Trp Phe Trp Trp Tyr Gly
                535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
                585                 590                 595

Gly Leu Val Gly Leu Lys Asp Gly Glu Met Lys Asn Phe Ser Ser Met
                600                 605                 610

Ser Pro Leu Ala Lys Gly Val Ser Val Tyr Phe Asp Gly Glu Gly Ile
615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
                665                 670                 675

Gly Leu Leu Ile Thr Lys His Val Val Tyr Glu Asn Gly Lys Ala Glu
                680                 685                 690

Ile Tyr Gly Ala Thr Asp Tyr Glu Lys Ser Glu Lys Leu Gly Glu Ala
                695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
                745                 750                 755

Thr Glu Val Lys Gly Val Val Ile Ala Asp Ile Thr Asp Pro Glu Gly
                760                 765                 770

Asp Asp His Gly Pro Gly Asn Tyr Thr Tyr Pro Thr Asp Lys Val Phe
                775                 780                 785

Lys Pro Gly Val Phe Asp Leu Leu Arg Phe Arg Met Leu Glu Gln Thr
790                 795                 800                 805

Glu Ser Tyr Val Met Glu Phe Tyr Phe Lys Asp Leu Gly Gly Asn Pro
                810                 815                 820

Trp Asn Gly Pro Asn Gly Phe Ser Leu Gln Ile Ile Glu Val Tyr Leu
                825                 830                 835

Asp Phe Lys Asp Gly Asn Ser Ser Ala Ile Lys Met Phe Pro Asp
                840                 845                 850

Gly Pro Gly Ala Asn Val Asn Leu Asp Pro Glu His Pro Trp Asp Val
                855                 860                 865

Ala Phe Arg Ile Ala Gly Trp Asp Tyr Gly Asn Leu Ile Ile Leu Pro
870                 875                 880                 885
```

```
Asn Gly Thr Ala Ile Gln Gly Glu Met Gln Ile Ser Ala Asp Pro Val
                890                 895                 900
Lys Asn Ala Ile Ile Val Lys Val Pro Lys Lys Tyr Ile Ala Ile Asn
            905                 910                 915
Glu Asp Tyr Gly Leu Trp Gly Asp Val Leu Val Gly Ser Gln Asp Gly
        920                 925                 930
Tyr Gly Pro Asp Lys Trp Arg Thr Ala Ala Val Asp Ala Glu Gln Trp
    935                 940                 945
Lys Leu Gly Gly Ala Asp Pro Gln Ala Val Ile Asn Gly Val Ala Pro
950                 955                 960                 965
Arg Val Ile Asp Glu Leu Val Pro Gln Gly Phe Glu Pro Thr Gln Glu
            970                 975                 980
Glu Gln Leu Ser Ser Tyr Asp Ala Asn Asp Met Lys Leu Ala Thr Val
        985                 990                 995
Lys Ala Leu Leu Leu Leu Lys Gln Gly Ile Val Val Thr Asp Pro
    1000                1005                1010
Glu Gly Asp  Asp His Gly Pro Gly Thr Tyr Thr Tyr Pro  Thr Asp
        1015                1020                1025
Lys Val Phe  Lys Pro Gly Val Phe Asp Leu Leu Lys Phe  Lys Val
        1030                1035                1040
Thr Glu Gly  Ser Asp Asp Trp Thr Leu Glu Phe His Phe  Lys Asp
        1045                1050                1055
Leu Gly Gly  Asn Pro Trp Asn Gly Pro Asn Gly Phe Ser  Leu Gln
        1060                1065                1070
Ile Ile Glu  Val Tyr Phe Asp Phe Lys Glu Gly Gly Asn  Val Ser
        1075                1080                1085
Ala Ile Lys  Met Phe Pro Asp Gly Pro Gly Ser Asn Val  Arg Leu
        1090                1095                1100
Asp Pro Asn  His Pro Trp Asp Leu Ala Leu Arg Ile Ala  Gly Trp
        1105                1110                1115
Asp Tyr Gly  Asn Leu Ile Ile Leu Pro Asp Gly Thr Ala  Tyr Gln
        1120                1125                1130
Gly Glu Met  Gln Ile Ser Ala Asp Pro Val Lys Asn Ala  Ile Ile
        1135                1140                1145
Val Lys Val  Pro Lys Lys Tyr Leu Asn Ile Ser Asp Tyr  Gly Leu
        1150                1155                1160
Tyr Thr Ala  Val Ile Val Gly Ser Gln Asp Gly Tyr Gly  Pro Asp
        1165                1170                1175
Lys Trp Arg  Pro Val Ala Ala Glu Ala Glu Gln Trp Lys  Leu Gly
        1180                1185                1190
Gly Ala Asp  Pro Gln Ala Val Ile Asp Asn Leu Val Pro  Arg Val
        1195                1200                1205
Val Asp Glu  Leu Val Pro Glu Gly Phe Lys Pro Thr Gln  Glu Glu
        1210                1215                1220
Gln Leu Ser  Ser Tyr Asp Leu Glu Lys Lys Thr Leu Ala  Thr Val
        1225                1230                1235
Leu Met Val  Pro Leu Val Asn Gly Thr Gly Gly Glu Glu  Pro Thr
        1240                1245                1250
Pro Thr Glu  Ser Pro Thr Glu Thr Thr Thr Thr Pro Ser  Glu
        1255                1260                1265
Thr Thr Thr  Thr Thr Ser Thr Thr Thr Gly Pro Ser Thr  Thr
        1270                1275                1280
Thr Ser Thr  Pro Gly Gly Gly Ile Cys Gly Pro Gly Ile  Ile Ala
```

-continued

```
            1285              1290              1295
Gly Leu Ala Leu Ile Pro Leu Leu Leu Lys Arg Arg Asn
        1300              1305              1310

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

Met Lys Lys Pro Leu Gly Lys Ile Val Ala Ser Thr Ala Leu Leu Ile
        -25              -20              -15

Ser Val Ala Phe Ser Ser Ser Ile Ala Ser Ala Glu Glu Pro Lys Pro
        -10               -5           -1  1               5

Leu Asn Val Ile Ile Val Trp His Gln His Gln Pro Tyr Tyr Tyr Asp
                10               15               20

Pro Ile Gln Asp Ile Tyr Thr Arg Pro Trp Val Arg Leu His Ala Ala
            25               30               35

Asn Asn Tyr Trp Lys Met Ala Asn Tyr Leu Ser Lys Tyr Pro Asp Val
            40               45               50

His Val Ala Ile Asp Leu Ser Gly Ser Leu Ile Ala Gln Leu Ala Asp
    55               60               65

Tyr Met Asn Gly Lys Lys Asp Thr Tyr Gln Ile Val Thr Glu Lys Ile
70               75               80               85

Ala Asn Gly Glu Pro Leu Thr Leu Glu Asp Lys Trp Phe Met Leu Gln
                90               95              100

Ala Pro Gly Gly Phe Phe Asp His Thr Ile Pro Trp Asn Gly Glu Pro
                105              110              115

Val Ala Asp Glu Asn Gly Asn Pro Tyr Arg Glu Gln Trp Asp Arg Tyr
            120              125              130

Ala Glu Leu Lys Asp Lys Arg Asn Asn Ala Phe Lys Lys Tyr Ala Asn
    135              140              145

Leu Pro Leu Asn Glu Gln Lys Val Lys Ile Thr Ala Glu Phe Thr Glu
150              155              160              165

Gln Asp Tyr Ile Asp Leu Ala Val Leu Phe Asn Leu Ala Trp Ile Asp
                170              175              180

Tyr Asn Tyr Ile Ile Asn Thr Pro Glu Leu Lys Ala Leu Tyr Asp Lys
            185              190              195

Val Asp Val Gly Gly Tyr Thr Lys Glu Asp Val Ala Thr Val Leu Lys
        200              205              210

His Gln Met Trp Leu Leu Asn His Thr Phe Glu Glu His Glu Lys Ile
    215              220              225

Asn Tyr Leu Leu Gly Asn Gly Asn Val Glu Val Thr Val Pro Tyr
230              235              240              245

Ala His Pro Ile Gly Pro Leu Leu Asn Asp Phe Gly Trp Tyr Glu Asp
            250              255              260

Phe Asp Ala His Val Lys Lys Ala His Glu Leu Tyr Lys Lys Tyr Leu
            265              270              275
```

-continued

Gly Asp Asn Arg Val Glu Pro Gln Gly Gly Trp Ala Ala Glu Ser Ala
            280                 285                 290

Leu Asn Asp Lys Thr Leu Glu Ile Leu Thr Asn Asn Gly Trp Lys Trp
        295                 300                 305

Val Met Thr Asp Gln Met Val Leu Asp Ile Leu Gly Ile Pro Asn Thr
310                 315                 320                 325

Val Glu Asn Tyr Tyr Lys Pro Trp Val Ala Glu Phe Asn Gly Lys Lys
                330                 335                 340

Ile Tyr Leu Phe Pro Arg Asn His Asp Leu Ser Asp Arg Val Gly Phe
                345                 350                 355

Arg Tyr Ser Gly Met Asn Gln Tyr Gln Ala Val Glu Asp Phe Val Asn
        360                 365                 370

Glu Leu Leu Lys Val Gln Lys Glu Asn Tyr Asp Gly Ser Leu Val Tyr
    375                 380                 385

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
            425                 430                 435

Tyr Gly Asp Lys Ala Asn Lys Leu Thr Pro Arg Met Met Glu Arg Leu
    440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
        520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
        600                 605                 610

Ser Pro Leu Ala Lys Gly Val Ser Val Tyr Phe Asp Gly Glu Gly Ile
    615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
        680                 685                 690

Ile Tyr Gly Ala Thr Asp Tyr Glu Lys Ser Glu Lys Leu Gly Glu Ala

```
                 695                 700                 705
Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
        760                 765                 770

Asp Asp His Gly Pro Gly Asn Tyr Thr
775                 780

<210> SEQ ID NO 13
<211> LENGTH: 546
<212> TYPE: PRT
<213> ORGANISM: Artificial Sequence
<220> FEATURE:
<223> OTHER INFORMATION: Alpha-amylase from Rhizomucor pusillus
      prepared from artificial DNA sequence

<400> SEQUENCE: 13

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270
```

```
Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Gly Ala Thr Ser Pro Gly Gly Ser Ser Gly
        435                 440                 445

Ser Val Glu Val Thr Phe Asp Val Tyr Ala Thr Thr Val Tyr Gly Gln
    450                 455                 460

Asn Ile Tyr Ile Thr Gly Asp Val Ser Glu Leu Gly Asn Trp Thr Pro
465                 470                 475                 480

Ala Asn Gly Val Ala Leu Ser Ser Ala Asn Tyr Pro Thr Trp Ser Ala
                485                 490                 495

Thr Ile Ala Leu Pro Ala Asp Thr Thr Ile Gln Tyr Lys Tyr Val Asn
            500                 505                 510

Ile Asp Gly Ser Thr Val Ile Trp Glu Asp Ala Ile Ser Asn Arg Glu
        515                 520                 525

Ile Thr Thr Pro Ala Ser Gly Thr Tyr Thr Glu Lys Asp Thr Trp Asp
    530                 535                 540

Glu Ser
545

<210> SEQ ID NO 14
<211> LENGTH: 583
<212> TYPE: PRT
<213> ORGANISM: Artificial Sequence
<220> FEATURE:
<223> OTHER INFORMATION: Alpha-amylase from Rhizomucor with SBD from
      Aspergillus niger prepared from artificial DNA sequence

<400> SEQUENCE: 14

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80
```

```
Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
            130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
            210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
            290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
            370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
            420                 425                 430

Ala Ile Phe Thr Ser Ala Thr Gly Thr Thr Thr Ala Thr Pro
            435                 440                 445

Thr Gly Ser Gly Ser Val Thr Ser Thr Ser Lys Thr Thr Ala Thr Ala
            450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495
```

```
Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
                580
```

<210> SEQ ID NO 15
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: Penicillium oxalicum glucoamylase (mature protein)

<400> SEQUENCE: 15

```
Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
                20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
                100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
                180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255
```

```
Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
        290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
        340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
        370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
        420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
        500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
        530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
        580                 585                 590

Trp Gln Phe
        595

<210> SEQ ID NO 16
<211> LENGTH: 412
<212> TYPE: PRT
<213> ORGANISM: Pyrococcus furiosus
<220> FEATURE:
<221> NAME/KEY: misc_feature
<223> OTHER INFORMATION: Pyrococcus furiosus protease

<400> SEQUENCE: 16

Ala Glu Leu Glu Gly Leu Asp Glu Ser Ala Ala Gln Val Met Ala Thr
1               5                   10                  15
```

```
Tyr Val Trp Asn Leu Gly Tyr Asp Gly Ser Gly Ile Thr Ile Gly Ile
            20                  25                  30
Ile Asp Thr Gly Ile Asp Ala Ser His Pro Asp Leu Gln Gly Lys Val
        35                  40                  45
Ile Gly Trp Val Asp Phe Val Asn Gly Arg Ser Tyr Pro Tyr Asp Asp
    50                  55                  60
His Gly His Gly Thr His Val Ala Ser Ile Ala Ala Gly Thr Gly Ala
65                  70                  75                  80
Ala Ser Asn Gly Lys Tyr Lys Gly Met Ala Pro Gly Ala Lys Leu Ala
                85                  90                  95
Gly Ile Lys Val Leu Gly Ala Asp Gly Ser Gly Ser Ile Ser Thr Ile
            100                 105                 110
Ile Lys Gly Val Glu Trp Ala Val Asp Asn Lys Asp Lys Tyr Gly Ile
        115                 120                 125
Lys Val Ile Asn Leu Ser Leu Gly Ser Ser Gln Ser Ser Asp Gly Thr
    130                 135                 140
Asp Ala Leu Ser Gln Ala Val Asn Ala Ala Trp Asp Ala Gly Leu Val
145                 150                 155                 160
Val Val Val Ala Ala Gly Asn Ser Gly Pro Asn Lys Tyr Thr Ile Gly
                165                 170                 175
Ser Pro Ala Ala Ala Ser Lys Val Ile Thr Val Gly Ala Val Asp Lys
            180                 185                 190
Tyr Asp Val Ile Thr Ser Phe Ser Ser Arg Gly Pro Thr Ala Asp Gly
        195                 200                 205
Arg Leu Lys Pro Glu Val Val Ala Pro Gly Asn Trp Ile Ile Ala Ala
    210                 215                 220
Arg Ala Ser Gly Thr Ser Met Gly Gln Pro Ile Asn Asp Tyr Tyr Thr
225                 230                 235                 240
Ala Ala Pro Gly Thr Ser Met Ala Thr Pro His Val Ala Gly Ile Ala
                245                 250                 255
Ala Leu Leu Leu Gln Ala His Pro Ser Trp Thr Pro Asp Lys Val Lys
            260                 265                 270
Thr Ala Leu Ile Glu Thr Ala Asp Ile Val Lys Pro Asp Glu Ile Ala
        275                 280                 285
Asp Ile Ala Tyr Gly Ala Gly Arg Val Asn Ala Tyr Lys Ala Ile Asn
    290                 295                 300
Tyr Asp Asn Tyr Ala Lys Leu Val Phe Thr Gly Tyr Val Ala Asn Lys
305                 310                 315                 320
Gly Ser Gln Thr His Gln Phe Val Ile Ser Gly Ala Ser Phe Val Thr
                325                 330                 335
Ala Thr Leu Tyr Trp Asp Asn Ala Asn Ser Asp Leu Asp Leu Tyr Leu
            340                 345                 350
Tyr Asp Pro Asn Gly Asn Gln Val Asp Tyr Ser Tyr Thr Ala Tyr Tyr
        355                 360                 365
Gly Phe Glu Lys Val Gly Tyr Tyr Asn Pro Thr Asp Gly Thr Trp Thr
    370                 375                 380
Ile Lys Val Val Ser Tyr Ser Gly Ser Ala Asn Tyr Gln Val Asp Val
385                 390                 395                 400
Val Ser Asp Gly Ser Leu Ser Gln Pro Gly Ser Ser
                405                 410
```

PROCESSES FOR PRODUCING FERMENTATION PRODUCTS

CROSS-REFERENCE TO RELATED APPLICATIONS

This application is a 35 U.S.C. 371 national application of PCT/US2012/059335 filed Oct. 9, 2012, which claims priority or the benefit under 35 U.S.C. 119 U.S. provisional application Nos. 61/545,865 and 61/566,165, filed Oct. 11, 2011 and Dec. 2, 2011, respectively, the contents of which are fully incorporated herein by reference.

FIELD OF THE INVENTION

The present invention relates to processes for producing fermentation products from starch-containing material. The invention also relates to compositions suitable for use in processes of the invention.

REFERENCE TO A SEQUENCE LISTING

This application contains a Sequence Listing in computer readable form, which is incorporated herein by reference.

BACKGROUND OF THE INVENTION

Production of fermentation products, such as ethanol, from starch-containing material is well-known in the art. Industrially two different kinds of processes are used today. The most commonly used process, often referred to as a "conventional process", including liquefying gelatinized starch at high temperature (typically between 80-90° C. at a pH between 5 and 6) using a bacterial alpha-amylase, followed by simultaneous saccharification and fermentation (SSF) carried out in the presence of a glucoamylase and a fermentation organism. Another well known process, often referred to as a "raw starch hydrolysis"-process (RSH process) includes simultaneously saccharifying and fermenting granular starch below the initial gelatinization temperature typically in the presence of an acid fungal alpha-amylase and a glucoamylase.

Despite significant improvements of fermentation product production processes over the past decade a significant amount of residual starch material is not converted into the desired fermentation product, such as ethanol. Therefore, there is still a desire and need for providing processes for producing fermentation products, such as ethanol, from starch-containing material that can provide a higher fermentation product yield compared to a conventional process.

SUMMARY OF THE INVENTION

The present invention relates to processes of producing fermentation products, such as especially ethanol, from starch-containing material using a fermenting organism.

In the first aspect the invention relates to processes for producing a fermentation product, such as ethanol, comprising the steps of:
   i) liquefying a starch-containing material at a temperature in the range from 60-80° C. using:
      a bacterial alpha-amylase;
      a raw starch hydrolyzing alpha-amylase;
      a carbohydrate-source generating enzyme having a heat stability at 70° C., pH 5.3, of at least 70%;
   ii) saccharifying using a carbohydrate-source generating enzyme;
   iii) fermenting using a fermenting organism.

In an embodiment also a protease, such as a metallo protease, is present and/or added during liquefaction in step i).

In an embodiment a pullulanase also is present and/or added during liquefaction in step i).

In an embodiment the bacterial alpha-amylase is derived from a strain of the genus Bacillus, preferably a strain of Bacillus stearothermophilus. The Bacillus stearothermophilus alpha-amylase may be truncated. In an embodiment the bacterial alpha-amylase is derived from Bacillus stearothermophilus (SEQ ID NO: 3 in WO 99/019467 or SEQ ID NO: 1 herein) which may be truncated to have about 491 amino acids. In an embodiment the Bacillus stearothermophilus alpha-amylase is truncated as indicated above and further has I181*+G182* deletions (relative to SEQ ID NO: 3 in WO 99/019467 or SEQ ID NO: 1 herein) or I181*+G182* deletions and a N193F substitution. In a preferred embodiment the bacterial alpha-amylase is derived from Bacillus stearothermophilus alpha-amylase (SEQ ID NO: 3 in WO 99/019467 or SEQ ID NO: 1 herein) which truncated, e.g., to have about 491 amino acids. The truncated Bacillus stearothermophilus alpha-amylase may also have mutations selected from the group consisting of:
   V59A+Q89R+E129V+K177L+R179E+I181*+G182*+N193F+H208Y+K220P+N224L+Q254S;
   E129V+K177L+R179E+I181*+G182*+N193F; and
   E129V+K177L+R179E+I181*+G182*+N193F+K220P+N224L+S242Q+Q254S.

In an embodiment the raw starch hydrolyzing alpha-amylase is of fungal origin. In a preferred embodiment the raw starch hydrolyzing alpha-amylase is derived from Rhizomucor pusillus with Aspergillus niger glucoamylase linker and SBD. In a specific embodiment the raw starch hydrolyzing alpha-amylase is a variant of Rhizomucor pusillus alpha-amylase with Aspergillus niger glucoamylase linker and SBD with further one or more of the following substitutions: G128D, D143N, K192R, such as G128D+D143N or G128D+D143N+K192R (using SEQ ID NO: 14 herein for the numbering).

In another embodiment the raw starch hydrolyzing alpha-amylase is derived from Aspergillus, such as Aspergillus niger alpha-amylase with Aspergillus kawachii linker and SBD or the Aspergillus kawachii alpha-amylase itself.

In an embodiment the carbohydrate-source generating enzyme present and/or added during liquefaction is different from the carbohydrate-source generating enzyme present and/or added during saccharification and/or fermentation.

Especially contemplated carbohydrate-source generating enzymes are glucoamylases. In a preferred embodiment the glucoamylase added during liquefaction is from the genus Penicillium, especially a strain of Penicillium oxalicum disclosed as SEQ ID NO: 2 in PCT/CN10/071,753 published as WO 2011/127802 (which is hereby incorporated by reference) and shown in SEQ ID NO: 9 or 15 herein, or a protease stable protein engineered variant of the Penicillium oxalicum glucoamylase disclosed in co-pending U.S. application No. 61/531,189 or U.S. application No. 61/566,046 or PCT/US12/053,779 having a K79V substitution.

In a preferred embodiment the carbohydrate-source generating enzyme is a variant of the Penicillium oxalicum glucoamylase disclosed as SEQ ID NO: 2 in PCT/CN10/071,753 published as WO 2011/127802 and shown in SEQ ID NO: 9 and 15 herein, having a K79V substitution (using the mature sequence shown in SEQ ID NO: 15 for numbering). The K79V glucoamylase variant has reduced sensitivity to protease degradation relative to the parent as disclosed in co-pending U.S. application No. 61/531,189 and U.S. application No. 61/566,046 or PCT/US12/053,779 (which are hereby incorporated by reference).

In a preferred embodiment the carbohydrate-source generating enzyme present and/or added during saccharification and/or fermentation, such as SSF, is a glucoamylase of fungal origin, preferably from a strain of *Aspergillus*, preferably *Aspergillus niger, Aspergillus awamori*, or *Aspergillus oryzae*; or a strain of *Trichoderma*, preferably *T. reesei*; or a strain of *Talaromyces*, preferably *T. emersonii*. In an embodiment the glucoamylase present and/or added during saccharification and/or fermentation may be derived from a strain of the genus *Pycnoporus*, in particular a strain of *Pycnoporus* as described in WO 2011/066576 (Novozymes), or from a strain of the genus *Gloephyllum*, in particular a strain of *Gloephyllum* as described in WO 2011/068803 (Novozymes) or a strain of the genus *Nigrofomes*, in particular a strain of *Nigrofomes* sp. disclosed in PCT/US10/058,375 published as WO 2012/064351 (Novozymes).

In a second aspect the invention relates to a composition comprising
  a bacterial alpha-amylase;
  a raw starch hydrolyzing alpha-amylase;
  a carbohydrate-source generating enzyme having a heat stability at 70° C., pH 5.3, of at least 70%.

In an embodiment of the invention a protease, such as a metallo protease, and/or a pullulanase is included in the composition. Other enzymes may also be included.

Examples of suitable bacterial alpha-amylases, raw starch hydrolyzing alpha-amylases and carbohydrate-source generating enzymes, especially glucoamylases, can be found below in the "Enzymes"-section.

BRIEF DESCRIPTION OF THE FIGURES

FIG. 1 shows the ethanol concentration after liquefaction at 75° C., pH 4.8, with *Bacillus stearothermophilus* alpha-amylase variant, raw starch hydrolyzing alpha-amylase variant derived from *Rhizomucor pusillus*, and *Penicillium oxalicum* glucoamylase variant followed by SSF for 54 hours using a *Talaromyces emersonii* glucoamylase and *Saccharomyces cerevisae* yeast.

DETAILED DESCRIPTION OF THE INVENTION

The present invention relates to processes of producing fermentation products, such as especially ethanol, from starch-containing material using a fermenting organism.

The inventors have shown that a process of the invention has a number of advantages. Example 5 shows that the yield is increased in an ethanol process where a combination of bacterial alpha-amylase, raw starch degrading alpha-amylase, and glucoamylase is present during liquefaction at 75° C., pH 4.8, followed by 54 hours simultaneous saccharification and fermentation (SSF) with *Saccharomyces cerevisae* yeast.

In the first aspect the invention relates to processes for producing fermentation products, such as ethanol, from starch-containing material comprising the steps of:
  i) liquefying the starch-containing material at a temperature in the range from 60-80° C. using:
    a bacterial alpha-amylase;
    a raw starch hydrolyzing alpha-amylase;
    a carbohydrate-source generating enzyme having a heat stability at 70° C., pH 5.3, of at least 70%;
  ii) saccharifying using a carbohydrate-source generating enzyme;
  iii) fermenting using a fermenting organism.

In an embodiment the process of the invention further comprises, prior to the liquefaction step i), the steps of:
  a) reducing the particle size of the starch-containing material, preferably by dry milling;
  b) forming a slurry comprising the starch-containing material and water.

The slurry may contain from 10-55 w/w-% dry solids (DS), preferably 25-45 w/w-% dry solids (DS), more preferably 30-40 w/w-% dry solids (DS) of starch-containing material.

The starch-containing material used as starting material is typically reduced in particle size, e.g., by milling, in order to open up the structure and allowing for further processing.

Generally there are two types of milling: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art. According to the invention dry milling is preferred. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The pH during liquefaction step i) is typically in the range from 4-6, preferably from 4.5-5.0 or 4.5-4.8 or between 5 and 6. The temperature during liquefaction may be in the range between from 70-80° C., such as between 75-80° C., preferably around 75° C. Typically the starch-containing material is heated during liquefaction step i) for 0.1-10 hours, such as 1-3 hours, such as around 1.5 hours.

The bacterial alpha-amylase, raw starch hydrolyzing alpha-amylase, and carbohydrate-source generating enzyme, in particular glucoamylase, and optional protease and/or pullulanase may be added to the aqueous slurry to initiate liquefaction (thinning). In an embodiment a part of the enzyme blend is added to the aqueous slurry, while the rest of the enzyme is added during liquefaction step i).

The aqueous slurry may in an embodiment be jet-cooked to further gelatinize the slurry before being subjected to liquefaction in step i). The jet-cooking may be carried out at a temperature between 95-145° C., such as 105-125° C., e.g., 110-145° C., preferably 120-140° C., such as 125-135° C., preferably around 130° C. for about 1-15 minutes, preferably for about 3-10 minutes, especially around about 5 minutes.

In an embodiment saccharification steps ii) and fermentation step iii) are carried out either sequentially or simultaneously. In a preferred embodiment steps ii) and iii) are carried out simultaneously (SSF process). In a preferred embodiment a carbohydrate-source generating enzyme, preferably a glucoamylase, is added. The carbohydrate-source generating enzyme, such as a glucoamylase, may be different from the enzyme added during liquefaction step i).

In an embodiment saccharification step ii) is carried out at a temperature from 20-75° C., preferably from 40-70° C., such as around 60° C., and at a pH between 4 and 5, such as around pH 4.5.

Further, fermentation step iii) or simultaneous saccharification and fermentation (SSF) may be carried out at a temperature from 25-40° C., such as from 28-35° C., such as from 30-34° C., preferably around about 32° C., wherein fermentation is ongoing for 6-120 hours, in particular 24-96 hours, such as around 54 hours.

Examples of suitable bacterial alpha-amylases can be found in the "Bacterial Alpha-Amylases" section below. In a preferred embodiment the bacterial alpha-amylase is a *Bacillus* alpha-amylase, preferably derived from a strain of *Bacillus stearothermophilus*, in particular the one shown in SEQ ID NO: 3 in WO 99/019467 or SEQ ID NO: 1 herein, such as one that is truncated, e.g., to have around 491 amino acids, e.g., from 485-495 amino acids. The *Bacillus stearothermophilus* alpha-amylase may also be a variant, e.g., one of the ones listed below and/or disclosed in WO 2011/082425 (hereby incorporated by reference).

Examples of raw starch hydrolyzing alpha-amylases can be found in the "Raw Starch Hydrolyzing Alpha-Amylases" section below. In an embodiment the raw starch hydrolyzing alpha-amylase is of fungal origin. In a preferred embodiment the raw starch hydrolyzing alpha-amylase is derived from *Rhizomucor pusillus* alpha-amylase and has an *Aspergillus niger* glucoamylase linker and SBD. In a preferred embodiment the raw starch hydrolyzing alpha-amylase is a variant of above further having one of the following substitutions: G128D+D143N or G128D+D143N+K192R (using SEQ ID NO: 14 herein for the numbering).

Examples of carbohydrate-source generating enzymes, including in particular glucoamylases, and can be found in the "Carbohydrate-Source Generating Enzymes" section below. The carbohydrate-source generating enzyme has a heat stability at 70° C., pH 5.3, of at least 70%, such as at least 75%, preferably at least 80%, preferably at least 85%.

In a preferred embodiment the glucoamylase is from the genus *Penicillium*, especially a strain of *Penicillium oxalicum* disclosed as SEQ ID NO: 2 in PCT/CN10/071,753 published as WO 2011/127802 (which is hereby incorporated by reference) and shown in SEQ ID NO: 9 and 15 herein or a protease stable protein engineered variant of the *Penicillium oxalicum* glucoamylase disclosed in co-pending U.S. application No. 61/531,189 or U.S. application No. 61/566,046 or PCT/US12/053,779 having a K79V substitution.

In an embodiment a protease is also present during liquefaction step i). Examples of proteases can be found in the "Proteases"-section below. In an embodiment the protease is a metallo protease. In an preferred embodiment the protease is derived from the genus *Thermoascus*, preferably a strain of *Thermoascus aurantiacus*, especially *Thermoascus aurantiacus* CGMCC No. 0670 (classified as EC 3.4.24.39) disclosed in SEQ ID NO: 3 herein or amino acids 1 to 177 (the mature polypeptide) of SEQ ID NO: 1 of WO 2010/008841.

Starch-Containing Materials

Any suitable starch-containing material may be used according to the present invention. The starting material is generally selected based on the desired fermentation product. Examples of starch-containing materials, suitable for use in processes of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley. Preferred starch-containing materials are corn and wheat.

Saccharification and Fermentation

One or more carbohydrate-source generating enzymes, in particular glucoamylases, are present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase.

Examples of carbohydrate-source generating enzymes, including glucoamylases, can be found in the "Carbohydrate-Source Generating Enzyme Present and/or Added During Saccharification and/or Fermentation"-section below.

When doing sequential saccharification and fermentation the saccharification in step ii) may be carried out using conditions well-known in the art. For instance, the saccharification step ii) may last up to from about 24 to about 72 hours. However, it is common to do only a pre-saccharification of typically 40-90 minutes at a temperature between 30-65° C., typically about 60° C., followed by saccharification during fermentation in simultaneous saccharification and fermentation (SSF). Saccharification may be carried out at temperatures from 20-75° C., preferably from 40-70° C., typically around 60° C., and at a pH between 4 and 5, normally at about pH 4.5.

Simultaneous saccharification and fermentation (SSF) is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" which refers to the environment in which fermentation is carried out and which includes the fermentation substrate, that is, the carbohydrate source that is metabolized by the fermenting organism. The fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, suitable for use for fermentation in a process of the invention. The fermenting organism is capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast, especially for ethanol production, includes strains of *Saccharomyces* spp., in particular, *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product is preferably ethanol. The fermentation products obtained according to the process of the invention may be ethanol. The fermentation product, such as especially ethanol, may be used as fuel which is typically blended with gasoline. However, in the case of ethanol it may also be used as potable ethanol. In a preferred embodiment the fermentation product is fuel ethanol.

Recovery

Subsequent to fermentation the fermentation product may be separated from the fermentation medium. The slurry may be distilled to extract the desired fermentation product. Alternatively the desired fermentation product may be extracted from the fermentation medium by micro or membrane filtration techniques. The fermentation product may also be recovered by stripping or other method well known in the art.

Enzymes

Bacterial Alpha-Amylases

According to the invention a bacterial alpha-amylase is present and/or added during liquefaction together of a raw starch hydrolyzing enzyme and a carbohydrate-source generating enzyme having a heat stability at 70° C., pH 5.3, of at least 70%, such as at least 75%, preferably at least 80%, preferably at least 85%.

Optionally a protease and/or a pullulanase is present or added during liquefaction as well.

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In a preferred embodiment the *Bacillus* alpha-amylase is derived from a strain of *Bacillus amyloliquefaciens*, *Bacillus licheniformis*, *Bacillus stearothermophilus*, or *Bacillus subtilis*, but may also be derived from other *Bacillus* sp.

Specific examples of bacterial alpha-amylases include the *Bacillus amyloliquefaciens* alpha-amylase of SEQ ID NO: 5 in WO 99/19467, the *Bacillus licheniformis* alpha-amylase of SEQ ID NO: 4 in WO 99/19467, and the *Bacillus stearothermophilus* alpha-amylase of SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NO: 3, 4 or 5, respectively, in WO 99/19467.

In an embodiment the bacterial alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% or at least 100% to any of the sequences shown in SEQ ID NO: 3 in WO 99/19467 or SEQ ID NO: 1 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), preferably corresponding to deletion of positions 181 and 182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 1 herein. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467 or SEQ ID NO: 1 herein. In a preferred embodiment the variant is a S242A, E or Q variant, preferably a S242Q variant of the *Bacillus stearothermophilus* alpha-amylase (using SEQ ID NO: 1 for numbering).

In an embodiment the variant has an E188 mutation, such as an E188P substitution in the *Bacillus stearothermophilus* alpha-amylase (using SEQ ID NO: 1 for numbering).

The bacterial alpha-amylase may in a preferred embodiment be a truncated *Bacillus licheniformis* alpha-amylase. Especially the truncation is so that the *Bacillus stearothermophilus* alpha-amylase shown in SEQ ID NO: 3 in WO 99/19467 or SEQ ID NO: 1 herein, is around 491 amino acids long.

Bacterial Hybrid Alpha-Amylases

The bacterial alpha-amylase may also be a hybrid bacterial alpha-amylase, e.g., an alpha-amylase comprising 445

C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:
G48A+T49I+G107A+H156Y+A181T+N190F+I201F+ A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In a preferred embodiment the bacterial alpha-amylase is the mature part of the chimeric alpha-amylase disclosed in Richardson et al., 2002, *The Journal of Biological Chemistry* 277(29): 26501-26507, referred to as BD5088 or a variant thereof. This alpha-amylase is the same as the one shown in SEQ ID NO: 2 in WO 2007/134207. The mature enzyme sequence starts after the initial "Met" amino acid in position 1.

In an embodiment the bacterial alpha-amylase is a thermostable bacterial alpha-amylase. In an embodiment the thermostable bacterial alpha-amylase is one disclosed in WO 2011/082425 (hereby incorporated by reference). In an embodiment the thermostable bacterial alpha-amylase is derived from a strain of the genus *Bacillus* (or *Geobacillus*), especially a strain of *Bacillus stearothermophilus*, in particular the *Bacillus stearothermophilus* as disclosed in WO 99/019467 as SEQ ID NO: 3 or SEQ ID NO: 1 herein, with the double deletion I181+G182 and substitution N193F, further comprising further mutations:

V59A+Q89R+G108A+E129V+K177L+R179E+ H208Y+K220P+N224L+Q254S+M284V;
V59A+Q89R+G112D+E129V+K177L+R179E+K220P+ N224L+Q254S;
V59A+Q89R+E129V+K177L+R179E+H208Y+K220P+ N224L+Q254S;
V59A+Q89R+E129V+K177L+R179E+H208Y+K220P+ N224L+Q254S+M284V;
V59A+Q89R+E129V+K177L+R179E+K220P+N224L+ Q254S+D269E+D281N;
V59A+Q89R+E129V+K177L+R179E+K220P+N224L+ Q254S+I270L;
V59A+Q89R+E129V+K177L+R179E+K220P+N224L+ Q254S+H274K;
V59A+Q89R+E129V+K177L+R179E+K220P+N224L+ Q254S+Y276F;
V59A+G108A;
V59A+G108A+E129V+K177L+R179E+H208Y+ K220P+N224L+S242Q+Q254S+M284V;
V59A+G108A+S242Q+M284V;
V59A+G108A+M284V;
V59A+E129V+R157Y+K177L+R179E+K220P+ N224L+S242Q+Q254S;
V59A+E129V+K177L+R179E+H208Y+K220P+ N224L+S242Q+Q254S;
V59A+E129V+K177L+R179E+H208Y+K220P+ N224L+S242Q+Q254S+M284V;
V59A+E129V+K177L+R179E+H208Y+M284V;
V59A+E129V+K177L+R179E+K220P+N224L+ S242Q+Q254S;
V59A+E129V+K177L+R179E+K220P+N224L+ S242Q+Q254S+H274K;
V59A+E129V+K177L+R179E+K220P+N224L+ S242Q+Q254S+Y276F;
V59A+E129V+K177L+R179E+K220P+N224L+ S242Q+Q254S+D281N;
V59A+E129V+K177L+R179E+K220P+N224L+ S242Q+Q254S+M284T;
V59A+E129V+K177L+R179E+K220P+N224L+ S242Q+Q254S+G416V;
V59A+E129V+K177L+R179E+K220P+N224L+Q254S;
V59A+E129V+K177L+R179E+K220P+N224L+ Q254S+M284T;
V59A+H208Y+K220P+N224L+Q254S+M284V;
V59A+M284V;
A91L+M96I+E129V+K177L+R179E+K220P+N224L+ S242Q+Q254S;
G108A+M284V;
E129V+K177L+R179E;
E129V+K177L+R179E+K220P+N224L+S242Q+ Q254S;
E129V+K177L+R179E+K220P+N224L+S242Q+ Q254S+Y276F+L427M;
E129V+K177L+R179E+K220P+N224L+S242Q+ Q254S+M284T;
E129V+K177L+R179E+K220P+N224L+S242Q+ Q254S+N376*+I377*;
E129V+K177L+R179E+K220P+N224L+Q254S;
E129V+K177L+R179E+K220P+N224L+Q254S+ M284T;
E129V+K177L+R179E+S242Q;
E129V+K177L+R179E+M284V;
E129V+K177L+R179V+K220P+N224L+S242Q+ Q254S;
K220P+N224L+S242Q+Q254S;
K220P+N224L+Q254S;
S242Q+M284V;
M284V.

In an embodiment the bacterial alpha-amylase variant may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99%, but less than 100% to any of the sequences shown in SEQ ID NO: 3 in WO 99/19467 or SEQ ID NO: 1 herein.

In an embodiment the bacterial alpha-amylase has a T½ (min) at pH 4.5, 75° C., 0.12 mM $CaCl_2$) of at least 20, such as at least 25, such as at least 30, such as at least 40, such as at least 50, such as at least 60, such as at least 70, such as at least 80, such as at least 90, such as at least 100, such as at least 110, such as at least 120, such as at least 130, such as at least 140, such as at least 150, such as at least 160, such as at least 170, such as at least 180 such as between 20-300, such as between 50-300, such as between 60-300, such as between 70-300, such as between 80-300, such as between 90-300, such as between 100-300, such as between 120-300, such as between 140-300 such as between 160-300, such as between 180-300.

The bacterial alpha-amylase is typically added in an amount between 0.0005-5 KNU per g DS, preferably between 0.001-1 KNU per g DS, such as around 0.06 KNU per g DS, or 0.0005-5 KNU(S) per g DS, preferably between 0.001-1 KNU(S) per g DS, such as around 0.060 KNU(S) per g DS if it is a *Bacillus stearothermophilus* alpha-amylase.

Examples of commercial compositions comprising bacterial alpha-amylases include BAN™, TERMAMYL™ SC, LIQUOZYME™ X, LIQUOZYME™ SC, (Novozymes), SPEZYME™ FRED, SPEZYME™ AA, SPEZYME™

DELTA AA, GC358, GC980, and SPEZYME™ RSL (Danisco A/S), and FUELZYME™ from Verenium, USA.

Raw Starch Hydrolyzing Alpha-Amylases

A raw starch hydrolyzing alpha-amylase is present during liquefaction step i) in a process of the invention together with a bacterial alpha-amylase and a carbohydrate-source generating enzyme having a heat stability at 70° C., pH 5.3, of at least 70%, such as at least 75%, preferably at least 80%, preferably at least 85%.

Optionally a protease and/or a pullulanase is present or added during liquefaction as well.

As used herein, a "raw starch hydrolyzing alpha-amylase" refers to an alpha-amylase that can directly degrade raw starch granules below the gelatinization temperature of starch. The gelatinization temperature of starch can range from 51° C. to 78° C. as the gelatinization initiation temperature can vary from about 51° C. to 68° C.

The raw starch hydrolyzing alpha-amylase may be of any origin. In a preferred embodiment the raw starch hydrolyzing alpha-amylase is derived from a fungal organism such as a filamentous fungus.

In an embodiment the raw starch hydrolyzing alpha-amylase is derived from a strain of *Aspergillus*, such as *Aspergillus niger* or *Aspergillus kawachii*.

In a preferred embodiment the fungal acid raw starch hydrolyzing alpha-amylase is a hybrid alpha-amylase.

In an embodiment the raw starch hydrolyzing enzyme is a hybrid enzyme which comprises an amino acid sequence of a catalytic module having alpha-amylase activity and an amino acid sequence of a carbohydrate-binding module, and optionally a linker, wherein the catalytic module is of fungal origin. Specific ensamples of such enzymes are the following enzymes disclosed especially tables 3 and 4 in WO 2005/003311. Raw starch hydrolyzing enzymes include the ones in the following table:

| Variant | Catalytic module | Linker | SBD |
|---|---|---|---|
| JA001 | Aspergillus niger AA (SP288) | Aspergillus kawachii AA | Aspergillus kawachii AA |
| JA002 | SP288 | A. kawachii AA | Aspergillus niger AMG |
| JA003 | SP288 | A. kawachii AA | Talaromyces emersonii AMG |
| JA004 | SP288 | A. kawachii AA | Athelia rolfsii AMG |
| JA005 | SP288 | A. kawachii AA | Bacillus MA |
| JA007 | Aspergillus kawachii AA | A. kawachii AA | A. kawachii AA |
| JA008 | SP288 | A. niger AMG | A. niger AMG |
| JA009 | SP288 | A. rolfsii AMG | A. niger AMG |
| JA010 | SP288 | PEPT | A. niger AMG |
| JA011 | SP288 | A. rolfsii AMG | A. rolfsii AMG |
| JA012 | SP288 | A. kawachii AA | A. niger AMG + A. rolfsii AMG |

In a preferred embodiment the raw starch hydrolyzing enzyme has the *Aspergillus niger* catalytic domain and an *Aspergillus kawachii* alpha-amylase (AA) or *Athelia rolfsii* glucoamylase (AMG) SBD.

In another preferred embodiment the raw starch degrading enzyme is *Aspergillus kawachii* alpha-amylase.

Specific examples of other contemplated raw starch hydrolyzing hybrid alpha-amylases include those disclosed in WO 2006/069290, especially the *Rhizomucor pusillus* alpha-amylase with *Athelia rolfsii* AMG linker and SBD (SEQ ID NO: 101 in U.S. application No. 60/638,614).

In a preferred embodiment the raw starch hydrolyzing alpha-amylase is the hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S).

Also contemplated is the *Meripilus giganteus* alpha-amylase with *Athelia rolfsii* glucoamylase linker and SBD (SEQ ID NO: 102 in U.S. application No. 60/638,614).

In another embodiment the raw starch hydrolyzing alpha-amylase is the hybrid alpha-amylase consisting of *Meripillus gigantus* alpha-amylase disclosed in WO 2006/069290 (Novozymes A/S).

The raw starch hydrolyzing alpha-amylases used in Example 5 herein are variants of the *Rhizomucor pusillus* alpha-amylase disclosed in co-pending U.S. provisional application No. 61/505,192 (which is hereby incorporated by reference).

RSH AA 96 is *Rhizomucor pusillus* alpha-amylase variant with *Aspergillus niger* glucoamylase linker and SBD and further the following substitutions: G128D+D143N (using SEQ ID NO: 14 herein for the numbering).

RSH AA 101 is *Rhizomucor pusillus* alpha-amylase variant with *Aspergillus niger* glucoamylase linker and SBD and further the following substitutions: G128D+D143N+K192R (using SEQ ID NO: 14 herein for the numbering).

In one embodiment, the raw starch hydrolyzing alpha-amylase is defined as an enzyme that has a raw starch degrading index of at least 0.2, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, at least 2, wherein the raw degrading index is a ratio of activity to degrade raw starch to activity to degrade gelatinized starch (Ra/Ga). Preferably, the raw starch hydrolyzing alpha-amylase is defined as an enzyme that has a raw starch degrading index of higher than 1. The activity on gelatinized starch is measured by measuring the release of glucose produced by the enzyme on a 2% gelatinized (e.g., corn) starch reaction mixture. The activity is measured by the release of reducing sugars produced in 4 mol per hour per mg of pure active enzyme. The same assay can then be used to measure the activity of the enzyme on raw starch, but substituting the 2% gelatinized (e.g., corn) starch by 2% of raw (e.g., corn) starch. In both assays, the temperature is 40° C., the same pH and buffer solution is used and the incubation time is 6 hours, and is further described in the "Materials and Methods" section below.

The raw starch hydrolyzing alpha-amylase for use in the present invention also include alpha-amylases having a high degree of sequence identity to the raw starch hydrolyzing alpha-amylases described herein. In an embodiment, the raw starch hydrolyzing alpha-amylase has sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, to the amino acid sequence of a raw starch hydrolyzing alpha-amylases disclosed herein. For example, raw starch hydrolyzing alpha-amylases include raw starch hydrolyzing alpha-amylases having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with the hybrid alpha-amylase disclosed as V039 in Table 5 in WO 2006/069290 or SEQ ID NOs: 13 or 14 herein.

In one embodiment, the raw starch hydrolyzing alpha-amylase may be added during liquefaction step i) in an amount of 0.01-1000 micro g Enzyme Protein (EP) per g DS, for example 0.1-500 micro g EP per g DS, such as 1-200 micro g EP per g DS, such as 1-100 micro g EP per g DS.

Carbohydrate-Source Generating Enzymes

According to the invention a carbohydrate-source generating enzyme having a heat stability at 70° C., pH 5.3, of at least 70%, such as at least 75%, preferably at least 80%, preferably at least 85%, preferably a glucoamylase, is present and/or added during liquefaction together with a bacterial alpha-amylase and a raw starch hydrolyzing alpha-amylase. A protease and/or a pullulanase may also be present and/or added during liquefaction step i).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In an embodiment the carbohydrate-source generating enzyme, preferably a glucoamylase, has a heat stability at 70° C., pH 5.3, of at least 70%, such as at least 75%, preferably at least 80%, preferably at least 85%.

In an embodiment the carbohydrate-source generating enzyme, preferably a glucoamylase, has a relative activity at pH 4.5 of at least 80%, preferably at least 85%, preferably at least 90% determined as described in Example 4 (pH Optimum).

In an embodiment the carbohydrate-source generating enzyme, preferably a glucoamylase, has a pH stability at pH 4.5 of at least at least 80%, at least 85%, at least 90%, at least 95%, at least 100% determined as described in Example 4 (pH Stability).

In a specific and preferred embodiment the carbohydrate-source generating enzyme is a glucoamylase, preferably of fungal origin, preferably a filamentous fungi, such as from a strain of the genus *Penicillium*, especially a strain of *Penicillium oxalicum* disclosed as SEQ ID NO: 2 in PCT/CN10/071,753 published as WO 2011/127802 (which is hereby incorporated by reference) and shown in SEQ ID NO: 9 herein or a *Penicillium oxalicum* variant disclosed in co-pending U.S. application No. 61/531,189 or U.S. application No. 61/566,046 or PCT/US12/053,779 having a K79V substitution (using SEQ ID NO: 15 herein for numbering). The K79V glucoamylase variant has reduced sensitivity to protease degradation compared to the parent.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071,753 published as WO 2011/127802 or SEQ ID NO: 9 herein.

Proteases

According to the invention a protease may be present and/or added during liquefaction in step i) together with a bacterial alpha-amylase, a raw starch hydrolyzing alpha-amylase and a carbohydrate-source generating enzyme, preferably a glucoamylase, having a heat stability at 70° C., pH 5.3, of at least 70%.

The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

The acid fungal protease may be derived from *Aspergillus, Candida, Coriolus, Endothia, Enthomophtra, Irpex, Mucor, Penicillium, Rhizopus, Sclerotium,* and *Torulopsis*. In particular, the protease may be derived from *Aspergillus aculeatus* (WO 95/02044), *Aspergillus awamori* (Hayashida et al., 1977, *Agric. Biol. Chem.* 42(5), 927-933), *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), or *Aspergillus oryzae*, such as the pepA protease; and acidic proteases from *Mucor miehei* or *Mucor pusillus*.

The protease may be a neutral or alkaline protease, such as a protease derived from a strain of *Bacillus*. A particular protease is derived from *Bacillus amyloliquefaciens* and has the sequence obtainable at Swissprot as Accession No. P06832. The proteases may have at least 90% sequence identity to the amino acid sequence disclosed in the Swissprot Database, Accession No. P06832 such as at least 92%, at least 95%, at least 96%, at least 97%, at least 98%, or particularly at least 99% identity.

The protease may have at least 75% identity, preferably at least 80%, more preferably at least 85%, more preferably at least 90% sequence identity to the amino acid sequence disclosed as SEQ ID NO: 1 in WO 2003/048353 or SEQ ID NO: 3 herein, such as at least 92%, at least 95%, at least 96%, at least 97%, at least 98%, or particularly at least 99% identity.

The protease may be a papain-like protease selected from the group consisting of proteases within EC 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment, the protease is a protease preparation derived from a strain of *Aspergillus*, such as *Aspergillus oryzae*. In another embodiment the protease is derived from a strain of *Rhizomucor*, preferably *Rhizomucor miehei*. In another embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei*.

Aspartic acid proteases are described in, for example, Handbook of Proteolytic Enzymes, Edited by A. J. Barrett, N. D. Rawlings and J. F. Woessner, Academic Press, San Diego, 1998, Chapter 270. Examples of aspartic acid proteases include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference.

The protease also may be a metallo protease, which is defined as a protease selected from the group consisting of: (a) proteases belonging to EC 3.4.24 (metalloendopeptidases); preferably EC 3.4.24.39 (acid metallo proteinases); (b) metallo proteases belonging to the M group of the above Handbook; (c) metallo proteases not yet assigned to clans (designation: Clan MX), or belonging to either one of clans MA, MB, MC, MD, ME, MF, MG, MH (as defined at pp. 989-991 of the above Handbook);

(d) other families of metallo proteases (as defined at pp. 1448-1452 of the above Handbook);
(e) metallo proteases with a HEXXH motif;
(f) metallo proteases with an HEFTH motif;
(g) metallo proteases belonging to either one of families M3, M26, M27, M32, M34, M35, M36, M41, M43, or M47 (as defined at pp. 1448-1452 of the above Handbook);
(h) metallo proteases belonging to the M28E family; and
(i) metallo proteases belonging to family M35 (as defined at pp. 1492-1495 of the above Handbook).

In other particular embodiments, metallo proteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metallo protease used in a process of the invention. In an embodiment the metallo protease is classified as EC 3.4.24, preferably EC 3.4.24.39. In one embodiment, the metallo protease is an acid-stable metallo protease, e.g., a fungal acid-stable metallo protease, such as a metallo protease derived from a strain of the genus *Thermoascus*, preferably a strain of *Thermoascus aurantiacus*, especially *Thermoascus aurantiacus* CGMCC No. 0670 (classified as EC 3.4.24.39). In another embodiment, the metallo protease is derived from a strain of the genus *Aspergillus*, preferably a strain of *Aspergillus oryzae*.

In one embodiment the metallo protease has a degree of sequence identity to amino acids −178 to 177, −159 to 177, or preferably amino acids 1 to 177 (the mature polypeptide) of SEQ ID NO: 1 of WO 2010/008841 or SEQ ID NO: 3 herein (a *Thermoascus aurantiacus* metallo protease) of at least 80%, at least 82%, at least 85%, at least 90%, at least 95%, or at least 97% such as at least 98%, such as at least 99%; and which have metallo protease activity. In particular embodiments, the metallo protease consists of an amino acid sequence with a degree of identity to SEQ ID NO: 1 as mentioned above or shown as SEQ ID NO: 3 herein.

The *Thermoascus aurantiacus* metallo protease is a preferred example of a metallo protease suitable for use in a process of the invention. Another metallo protease is derived from *Aspergillus oryzae* and comprises the sequence of SEQ ID NO: 11 disclosed in WO 2003/048353, or amino acids −23-353; −23-374; −23-397; 1-353; 1-374; 1-397; 177-353; 177-374; or 177-397 thereof, and SEQ ID NO: 10 disclosed in WO 2003/048353.

Another metallo protease suitable for use in a process of the invention is the *Aspergillus oryzae* metallo protease comprising SEQ ID NO: 5 of WO 2010/008841, or a metallo protease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metallo protease consists of the amino acid sequence of SEQ ID NO: 5 of WO 2010/008841 (hereby incorporated by reference).

In a particular embodiment, a metallo protease has an amino acid sequence that differs by forty, thirty-five, thirty, twenty-five, twenty, or by fifteen amino acids from amino acids −178 to 177, −159 to 177, or +1 to 177 of the amino acid sequences of the *Thermoascus aurantiacus* or *Aspergillus oryzae* metallo protease.

In another embodiment, a metallo protease has an amino acid sequence that differs by ten, or by nine, or by eight, or by seven, or by six, or by five amino acids from amino acids −178 to 177, −159 to 177, or +1 to 177 of the amino acid sequences of these metallo proteases, e.g., by four, by three, by two, or by one amino acid.

In particular embodiments, the metallo protease a) comprises or b) consists of
i) the amino acid sequence of amino acids −178 to 177, −159 to 177, or +1 to 177 of SEQ ID NO:1 of WO 2010/008841;
ii) the amino acid sequence of amino acids −23-353, −23-374, −23-397, 1-353, 1-374, 1-397, 177-353, 177-374, or 177-397 of SEQ ID NO: 3 of WO 2010/008841;
iii) the amino acid sequence of SEQ ID NO: 5 of WO 2010/008841; or
allelic variants, or fragments, of the sequences of i), ii), and iii) that have protease activity.

A fragment of amino acids −178 to 177, −159 to 177, or +1 to 177 of SEQ ID NO: 1 of WO 2010/008841 or of amino acids −23-353, −23-374, −23-397, 1-353, 1-374, 1-397, 177-353, 177-374, or 177-397 of SEQ ID NO: 3 of WO 2010/008841; is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

In another embodiment, the metallo protease is combined with another protease, such as a fungal protease, preferably an acid fungal protease.

Commercially available products include ALCALASE®, ESPERASE™, FLAVOURZYME™, NEUTRASE®, RENNILASE®, NOVOZYM™ FM 2.0 L, and iZyme BA (available from Novozymes A/S, Denmark) and GC106™ and SPEZYME™ FAN from Genencor International, Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment the protease used in a process of the invention is a thermostable protease. Preferably one disclosed in WO 2011/072191 (hereby incorporated by reference) which may have either
i) a thermostability value of more than 20% determined as Relative Activity at 80° C./70° C.; and/or
ii) a thermostability value of more than 10% determined as Relative Activity at 85° C./70° C.

In an embodiment the protease has a thermostability value:
of more than 30%, more than 40%, more than 50%, more than 60%, more than 70%, more than 80%, more than 90% determined as Relative Activity at 80° C./70° C., and/or
of more than 12%, more than 14%, more than 16%, more than 18%, more than 20%, determined as Relative Activity at 85° C./70° C.; and/or
of more than 20%, more than 30%, more than 40%, more than 50%, more than 60%, more than 70%, more than 80%, more than 90% determined as Remaining Activity at 80° C.; and/or
of more that 20%, more than 30%, more than 40%, more than 50%, more than 60%, more than 70%, more than 80%, more than 90% determined as Remaining Activity at 84° C. and/or.

Purified variants may have a thermostability for above 90, above 100 at 85° C. as determined using the Zein-BCA assay as disclosed in Example 3.

Determination of "Relative Activity" and "Remaining Activity" is determined as described in Example 2.

In a preferred embodiment the thermostable protease used in a process of the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the protease has at least 20%, such as at least 30%, such as at least 40%, such as at least 50%, such as at least 60%, such as at least 70%, such as at least 80%, such as at least 90%, such as at least 100% of the activity of the JTP196 protease variant or Protease Pfu determined by the AZCL-casein assay.

There are no limitations on the origin of the thermostable protease used in a process of the invention as long as it fulfills the thermostability properties defined above. The protease may be a variant of, e.g., a wild-type protease as long as the protease has the thermostability properties defined above. In a preferred embodiment the protease is a variant of a metallo protease as defined above. In an embodiment the protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the protease is a variant of the mature part of the metallo protease shown in SEQ ID NO: 2 disclosed in WO 2003/048353 or the mature part of SEQ ID NO: 1 in WO 2010/008841 and shown as SEQ ID NO: 3 herein with the following mutations:

S5*+N26R+D79L+S87P+A112P+D142L;
S5*+D79L+S87P+A112P+D142L;
N26R+T46R+D79L+S87P+A112P+D142L;
A27K+D79L+Y82F+S87G+D104P+A112P+A126V+D142L;
A27K+D79L+Y82F+D104P+A112P+A126V+D142L;
A27K+Y82F+S87G+D104P+A112P+A126V+D142L;
A27K+D79L+S87P+A112P+T124V+D142L;
A27K+D79L+S87P+A112P+A126V+D142L;
A27K+D79L+S87P+A112P+D142L.
A27K+Y82F+D104P+A112P+A126V+D142L;
S36P+D79L+S87P+A112P+D142L;
A37P+D79L+S87P+A112P+D142L;
S38T+D79L+S87P+A112P+A126V+D142L;
T46R+D79L+S87P+T116V+D142L;
S49P+D79L+S87P+A112P+D142L;
S50P+D79L+S87P+A112P+D142L;
S70V+D79L+Y82F+S87G+Y97W+A112P+D142L;
S70V+D79L+Y82F+S87G+A112P+D142L;
D79L+P81R+S87P+A112P+D142L;
D79L+Y82F+S87G+Y97W+D104P+A112P+D142L;
D79L+Y82F+S87G+D104P+A112P+D142L;
D79L+Y82F+S87G+A112P+A126V+D142L;
D79L+Y82F+S87G+A112P+D142L;
D79L+Y82F+S87P+A112P+T124V+D142L;
D79L+Y82F+S87P+A112P+A126V+D142L;
D79L+Y82F+S87P+A112P+D142L;
D79L+S87P+N98C+A112P+G135C+D142L;
D79L+S87P+D104P+A112P+D142L;
D79L+S87P+A112P+T124V+A126V+D142L;
D79L+S87P+A112P+T124V+D142L;
D79L+S87P+A112P+D142L;
D79L+S87P+A112P+D142L+T141C+M161C;
Y82F+S87G+S70V+D79L+D104P+A112P+D142L;
Y82F+S87G+D79L+D104P+A112P+A126V+D142L.

In an embodiment the thermostable protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

In an embodiment the protease is derived from a strain of *Pyrococcus*, such as a strain of *Pyrococcus furiosus*. In an embodiment the protease is the one shown as SEQ ID NO: 1 in U.S. Pat. No. 6,358,726-B1 (Takara Shuzo Company). In another embodiment the protease is one disclosed in SEQ ID NO: 16 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 16 herein. The *Pyroccus furiosus* protease can be purchased from Takara Bio, Japan.

The *Pyrococcus furiosus* protease is a thermostable protease. The commercial *Pyrococcus furiosus* protease product (Pfu S) from Takara Bio, Japan was found to have a thermostability of 110% (80° C./70° C.) and 103% (90° C./70° C.) at pH 4.5 determined as described in Example 2 herein.

Pullulanase

According to the invention a pullulanase may further be present during liquefaction, saccharification and/or fermentation.

In an embodiment a pullulanase is present and/or added during liquefaction step i).

In another embodiment a pullulanase is present and/or added during saccharification or simultaneous saccharification and fermentation (SSF).

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

The pullulanase may be any pullulanase. In an embodiment the pullulanase is a bacterial pullulanase, especially a pullulanase derived from a strain on the genus *Bacillus*, especially derived from a strain of *Bacillus deramificans*. EP 605,040 discloses such pullulanase derived from *Bacillus deramificans*.

In an embodiment the pullulanase is a variant disclosed in WO 00/01796. Contemplated pullulanases include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in *FEMS Mic. Let.* 115: 97-106 (1994).

Additional pullulanases contemplated according to the present invention included the pullulanases from *Pyrococcus woesei*, specifically from *Pyrococcus woesei* DSM No. 3773 disclosed in WO 92/02614.

In an embodiment the pullulanase is a family GH57 pullulanase. In an embodiment the pullulanase includes an X47 domain as disclosed in WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown in SEQ ID NO: 11 truncated at site X4 right after the X47 domain (i.e., amino acids 1-782 in SEQ ID NOS: 11 and 12). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in WO 2011/087836 (which is hereby incorporated by reference) or disclosed in SEQ ID NO: 12 herein.

In another embodiment the pullulanase is derived from a strain of *Thermococcus*, such as especially *Thermococcus hydrothermalis*. In an embodiment the pullulanase is a variant of *Thermococcus hydrothermalis*. In an embodiment the pullulanase comprises X47 domain. In an embodiment the pullulanase is truncated, such as one disclosed in WO 2011/087836. In an embodiment the pullulanase comprises an X46 domain such as one disclosed in WO 2011/076123.

The pullulanases added during liquefaction and saccharification and/or fermentation may not be the same. For instance, in an embodiment the pullulanase present and/or added during liquefaction step i) is derived from *Thermococcus hydrothermalis*, while the pullulanase optionally added during saccharification and/or fermentation is derived from *Bacillus deramificans*. Pullulanase activity may be determined as NPUN. An Assay for determination of NPUN is described in the "Materials & Methods"-section below.

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Commercially available pullulanase products include PROMOZYME D, PROMOZYME™ D2 (Novozymes A/S, Denmark), OPTIMAX L-300 (Danisco, USA), and AMANO 8 (Amano, Japan).

Carbohydrate-Source Generating Enzyme Present and/or Added During Saccharification and/or Fermentation According to the invention a carbohydrate-source generating enzyme, preferably a glucoamylase, may be present and/or added during saccharification and/or fermentation. The carbohydrate-source generating enzyme may be different from the carbohydrate-source generating enzyme, preferably glucoamylase, present and/or added during liquefaction step i).

Glucoamylase

According to the invention the glucoamylase present and/or added during saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, EMBO J. 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (*Agric. Biol. Chem.* 55(4): 941-949 (1991)), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in position A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and (Nagasaka et al., 1998, "Purification and properties of the raw-starch-degrading glucoamylases from *Corticium rolfsii, Appl. Microbiol. Biotechnol.* 50:323-330), *Talaromyces* glucoamylases, in particular derived from *Talaromyces emersonii* (WO 99/28448), *Talaromyces leycettanus* (U.S. Pat. No. RE32,153), *Talaromyces duponti*, *Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

In an embodiment the glucoamylase is a glucoamylase which exhibits at least 70%, at least 75%, at least 80%, at least 85%, at least 90%, at least 95%, at least 96%, at least 97%, at least 98%, at least 99% or even 100% identity to the mature enzyme sequence shown as SEQ ID NO: 7 in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831) and *Trametes cingulata, Pachykytospora papyracea*; and *Leucopaxillus giganteus* all disclosed in WO 2006/069289; or *Peniophora rufomarginata* disclosed in WO 2007/124285; or a mixture thereof. Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (Novozymes), or from a strain of the genus *Gloephyllum*, in particular a strain of *Gloephyllum* as described in WO 2011/068803 (Novozymes) or a strain of the genus *Nigrofomes*, in particular a strain of *Nigrofomes* sp. disclosed in PCT/US10/058,375 published as WO 2012/064351 (Novozymes).

Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

In an embodiment the glucoamylase is a glucoamylase which exhibits at least 70%, at least 75%, at least 80%, at least 85%, at least 90%, at least 95%, at least 96%, at least 97%, at least 98%, at least 99% or even 100% identity to the mature enzyme sequences shown in any one of SEQ ID NO: 2, 4 or 6 in WO 2011/066576.

In an embodiment the glucoamylase is a glucoamylase which exhibits at least 70%, at least 75%, at least 80%, at least 85%, at least 90%, at least 95%, at least 96%, at least 97%, at least 98%, at least 99% or even 100% identity to the mature enzyme sequences shown in any one of SEQ ID NO: 2, 4, 6, 8, 10, 12, 14, 16 or 18 in WO 2011/068803.

Carbohydrase-source generating enzymes, such as preferably glucoamylases, may in an embodiment be added in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200 L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Genencor Int.).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from Bacillus stearothermophilus strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Composition Comprising Bacterial Alpha-Amylase, Raw Starch Hydrolyzing Alpha-Amylase and Carbohydrate-Source Generating Enzyme.

Compositions of the invention may be added during liquefaction step i) in a process of the invention. Compositions of the invention comprise a bacterial alpha-amylase, a raw starch hydrolyzing alpha-amylase and carbohydrate-source generating enzyme. The composition may further comprise a protease and/or a pullulanase and other enzymes.

Thus, in this aspect the invention relates to composition comprising a bacterial alpha-amylase;
a raw starch hydrolyzing alpha-amylase;
carbohydrate-source generating enzyme having a heat stability at 70° C., pH 5.3, of at least 70%.

In an embodiment the bacterial alpha-amylase is derived from a starch of Bacillus. Suitable bacterial alpha-amylases are described in the "Bacterial Alpha-Amylase" section above.

In an embodiment the bacterial alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

In a preferred embodiment the bacterial alpha-amylase is derived from Bacillus stearothermophilus alpha-amylases, especially a variant which comprising have a double deletion corresponding to a deletion of positions 181 and 182 and further comprise a N193F substitution (also denoted I181*+G182*+N193F). The Bacillus stearothermophilus alpha-amylases may be a variants disclosed in disclosed in WO 2011/082425 or below specifically disclosed.

Preferred bacterial alpha-amylases are derived from the Bacillus stearothermophilus alpha-amylase shown in SEQ ID NO: 1 herein truncated to have about 491 amino acids with the mutations selected from the group consisting of:

V59A+Q89R+E129V+K177L+R179E+I181*+G182*+ N193F+H208Y+K220P+N224L+Q254S;

E129V+K177L+R179E+I181*+G182*+N193F; and

E129V+K177L+R179E+I181*+G182*+N193F+K220P+ N224L+S242Q+Q254S.

In an embodiment the bacterial alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

Suitable raw starch hydrolyzing enzymes are described in the "Raw Starch Hydrolyzing Alpha-Amylase" section above.

In an embodiment the raw starch hydrolyzing alpha-amylase is of fungal origin. In a preferred embodiment the raw starch hydrolyzing alpha-amylase is a variant of Rhizomucor pusillus alpha-amylase with Aspergillus niger glucoamylase linker and SBD and further one or more of the following substitutions: G128D, D143N, K192R, such as especially G128D+D143N or G128D+D143N+K192R (using SEQ ID NO: 14 herein for the numbering).

Suitable carbohydrate-source generating enzymes, preferably glucoamylases, are described in the "Carbohydrate-Source Generating Enzymes" section above.

In an embodiment the carbohydrate-source generating enzyme is a glucoamylase having a heat stability at 70° C., pH 5.3, of at least 70% such as at least 75%, preferably at least 80%, preferably at least 85, is a glucoamylase. In a preferred embodiment the glucoamylase is from the genus Penicillium, especially a strain of Penicillium oxalicum disclosed as SEQ ID NO: 2 in PCT/CN10/071,753 published as WO 2011/127802 (which is hereby incorporated by reference) and shown in SEQ ID NO: 9 herein or a protease stable protein engineered variant(s) of the Penicillium oxalicum glucoamylase disclosed in co-pending U.S. application No. 61/531,189 or U.S. application No. 61/566,046 or PCT/US12/053,779 (Novozymes) having a K79V substitution (using SEQ ID NO: 15 herein for numbering).

In another embodiment the carbohydrate-source generating enzyme is the glucoamylase shown in SEQ ID NO: 9 or a glucoamylase having at least 80%, such as at least 90%, such as at least 95%, such as at least 96%, such as at least 97%, such as at least 98%, such as at least 99% identity SEQ ID NO: 9 herein.

In an embodiment the composition further comprises a protease. The protease may be of fungal or bacterial origin. Suitable proteases are described in the "Protease" section above.

In an embodiment the protease is a metallo protease. In an embodiment the protease is derived from the genus *Thermoascus*, preferably a strain of *Thermoascus aurantiacus*, especially *Thermoascus aurantiacus* CGMCC No. 0670 (classified as EC 3.4.24.39) disclosed in SEQ ID NO: 3 herein or amino acids 1 to 177 (the mature polypeptide) of SEQ ID NO: 1 of WO 2010/008841.

In an embodiment protease is derived from a strain of *Pyrococcus*, preferably a strain of *Pyrococcus furiosus*, such as the one shown in SEQ ID NO: 1 in U.S. Pat. No. 6,258,726 or SEQ ID NO: 16 herein.

In an embodiment the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,258,726 or SEQ ID NO: 16 herein.

In an embodiment the composition of the invention comprises
- a bacterial alpha-amylase derived from *Bacillus stearothermophilus*;
- a raw starch hydrolyzing alpha-amylase derived from *Rhizomucor pusillus*;
- a carbohydrate-source generating enzyme having a heat stability at 70° C., pH 5.3, of at least 70% derived from *Penicillium oxalicum*.

In an embodiment the composition further comprises a protease derived from *Thermoascus aurantiacus* or *Pyrococcus furiosus*.

In an embodiment the composition further comprises a pullulanase. Suitable pullulanases are described in the "Pullulanase"-section above.

In an embodiment the pullulanase is derived from the genus *Thermococcus*, such as a strain of *Thermococcus hydrothermalis* pullulanase shown in SEQ ID NO: 11 truncated right after the X47 domain (i.e., amino acids 1-782 in SEQ ID NO: 11).

Materials & Methods
Materials:
Reference Alpha-Amylase A:
  *Bacillus stearothermophilus* alpha-amylase with the mutations I181*+G182*+N193F truncated to 491 amino acids (using SEQ ID NO: 1 herein for numbering)
Alpha-Amylase (BAA 1407):
  *Bacillus stearothermophilus* alpha-amylase with the mutations: V59A+Q89R+E129V+K177L+R179E+I181*+G182*+N193F+H208Y+K220P+N224L+Q254S truncated to 491 amino acids (using SEQ ID NO: 1 herein for numbering).
Alpha-Amylase (RSH AA 96):
  Hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S) or SEQ ID NO: 14 herein with the following substitutions: G128D+D143N.
Alpha-Amylase (RSH AA 101):
  Hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S) or SEQ ID NO: 14 herein with the following substitutions: G128D+D143N+K192R.
Glucoamylase (AMG 001):
  Mature part of the *Penicillium oxalicum* glucoamylase disclosed as SEQ ID NO: 2 in PCT/CN10/071,753 published as WO 2011/127802 and shown in SEQ ID NO: 9 and 15 herein with a K79V substitution (using SEQ ID NO: 15 herein for numbering) as disclosed in co-pending U.S. application No. 61/531,189.
Glucoamylase (AMG SPU):
  *Tamaromyces emersonii* glucoamylase disclosed in WO 99/28448 with about 20% glucoamylase activity from *Trametes cingulata* glucoamylase disclosed in WO 06/069289 and side activity from hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S) or SEQ ID NO: 14 herein.
Corn:
  Ground corn and backset used in Example 5 were obtained from Corn LP in November of 2010 The dry solids (% DS) contents of the ground corn and backset were measured to be 86.78 and 7.93%, respectively, by oven drying at 105° C. for 3 hours.
Yeast:
  RED STAR ETHANOL RED™ available from Red Star/Lesaffre, USA.

Methods
Identity:
The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see Pearson and Lipman, 1988, "Improved Tools for Biological Sequence Analysis", *PNAS* 85:2444-2448, and Pearson, 1990, "Rapid and Sensitive Sequence Comparison with FASTP and FASTA," *Methods in Enzymology* 183:63-98). FASTA protein alignments use the Smith-Waterman algorithm with no limitation on gap size (see "Smith-Waterman algorithm", Smith and Waterman, 1981, *J. Mol. Biol.* 147: 195-197).

Protease Assays
AZCL-Casein Assay
A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay
50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ca$^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

KNU(S) Alpha-Amylase Activity

KNU(S) is used to determine the activity of *Bacillus stearothermophilus* alpha-amylase and is described on page 35-41 in WO 99/19467 (hereby incorporated by reference).

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

Raw Starch Degrading Enzyme (Ra/Ga) Assay

A protocol to obtaining a raw starch degrading enzyme index (Ra/Ga) value is as follows:

1) The assays are performed at a temperature of 40° C.
2) First, the pH profile of the enzyme is obtained on raw starch. The profile is obtained from the plotting of the % activity versus the pH. This optimum pH value is used in the assay.
3) Any type of starch may be used, such as, wheat, corn, barley, rice, etc. In an example, the raw starch used is corn starch. A 2% solution of raw starch is used. Alternatively, to obtain the gelatinized starch solution, a solution of raw starch is heated above the gelatinization temperature for at least 60 minutes. In the case of corn, the solution of raw starch is heated to 70° C. for at least 60 minutes.
4) The reaction solution contains the gelatinized starch (or raw starch) and a buffer. The composition of the buffer used in the assay depends on the pH optimum of the enzyme. The buffer composition and concentration must be identical for both the raw and gelatinized starch activity measurements.
5) The enzyme concentration used in the assay must be identical for both the raw and gelatinized starch activity measurements.
6) The enzyme activity is measured by determination of the reducing sugars in solution. Suitable methods are the following: The method of Bernfield for determining reducing sugars using dinitrosalicylic acid is described in Bernfield, 1955, *Methods Enzymology* 1:149-158 and the method for determining reducing sugars with copper-bicinchoninate as described in Fox et al., 1991, *Analytical Biochemistry* 195: 93-96 or in Waffenschmidt et al., 1987, *Anal. Biochem.* 165: 337-340. Prior to the determination of reducing sugars, the solutions are boiled for 3 minutes and centrifugated to inactivate the enzyme.
7) The time for incubation to measure the enzyme activities is 6 hours.
8) The enzyme activity is expressed as the number reducing sugars produced per hour and per mg of pure active enzyme.
9) The activity on gelatinized starch is measured by measuring the release of glucose produced by the enzyme on a 2% gelatinized (e.g., corn) starch reaction mixture and the activity on raw starch is measured by measuring the release of glucose produced by the enzyme on a 2% raw (e.g., corn) starch reaction mixture. The activity is measured by the release of reducing sugars produced in 4 mol per hour per mg of pure active enzyme.

EXAMPLES

Example 1

Stability of Alpha-Amylase Variants

The stability of a reference alpha-amylase (*Bacillus stearothermophilus* alpha-amylase with the mutations I181*+G182*+N193F truncated to 491 amino acids (using SEQ ID NO: 1 herein for numbering) and alpha-amylase variants thereof was determined by incubating the reference alpha-amylase and variants at pH 4.5 and 5.5 and temperatures of 75° C. and 85° C. with 0.12 mM CaCl₂ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM CaCl₂, pH 5.0). Twenty microliters enzyme sample was transferred to 48-well PCR MTP and 180 microliters stability buffer (150 mM acetate, 150 mM MES, 0.01% Triton X100, 0.12 mM CaCl₂, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM CaCl₂, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T½ (min)=T(min)*LN(0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl₂) | T½ (min) (pH 4.5, 85° C., 0.12 mM CaCl₂) | T½ (min) (pH 5.5, 85° C., 0.12 mM CaCl₂) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |

TABLE 1-continued

| Mutations | T½ (min) (pH 4.5, 75° C., 0.12 mM CaCl₂) | T½ (min) (pH 4.5, 85° C., 0.12 mM CaCl₂) | T½ (min) (pH 5.5, 85° C., 0.12 mM CaCl₂) |
|---|---|---|---|
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Preparation of Protease Variants and Test of Thermostability

Chemicals used were commercial products of at least reagent grade.

Strains and Plasmids:

*E. coli* DH12S (available from Gibco BRL) was used for yeast plasmid rescue. pJTP000 is a *S. cerevisiae* and *E. coli* shuttle vector under the control of TPI promoter, constructed from pJC039 described in WO 01/92502, in which the *Thermoascus aurantiacus* M35 protease gene (WO 03/048353) has been inserted.

*Saccharomyces cerevisiae* YNG318 competent cells: MATa Dpep4[cir+] ura3-52, leu2-D2, h is 4-539 was used for protease variants expression. It is described in *J. Biol. Chem.* 272(15): 9720-9727 (1997).

Media and Substrates

10× Basal Solution:

Yeast nitrogen base w/o amino acids (DIFCO) 66.8 g/L, succinate 100 g/l, NaOH 60 g/l.

SC-Glucose:

20% glucose (i.e., a final concentration of 2%=2 g/100 mL)) 100 mL/L, 5% threonine 4 mL/L, 1% tryptophan 10 ml/l, 20% casamino acids 25 ml/l, 10× basal solution 100 ml/l. The solution is sterilized using a filter of a pore size of 0.20 micrometer. Agar (2%) and H₂O (approx. 761 mL) is autoclaved together, and the separately sterilized SC-glucose solution is added to the agar solution.

YPD:

Bacto peptone 20 g/l, yeast extract 10 g/L, 20% glucose 100 mL/L.

YPD+Zn:

YPD+0.25 mM ZnSO₄.

PEG/LiAc solution:

40% PEG4000 50 ml, 5 M Lithium Acetate 1 mL.

96 Well Zein Micro Titre Plate:

Each well contains 200 microL of 0.05-0.1% of zein (Sigma), 0.25 mM ZnSO₄ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "*Current protocols in Molecular Biology*", John Wiley and Sons, 1995; Harwood, C. R. and Cutting, S. M. (Eds.).

Yeast Transformation

Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 mL polypropylene tube (Falcon 2059). Add 0.6 mL PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 mL of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The *Themoascus* M35 protease gene was amplified with the primer pair Prot F (SEQ ID NO: 4) and Prot R (SEQ ID NO: 5). The resulting PCR fragments were introduced into *S. cerevisiae* YNG318 together with the pJC039 vector (described in WO 2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 6) and AM35 (SEQ ID NO:7) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL H$_2$O | 1 | 94° C. 2 min |
| 2 beads puRe Taq Ready-To-Go PCR (Amersham Biosciences) | 2 | 94° C. 30 sec |
| 0.5 microL × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 mL of 12.5% azo-casein in ethanol in 96 mL of 20 mM sodium acetate, pH 4.5, containing 0.01% triton-100 and 0.25 mM ZnSO$_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al., 2001, *Appl. Environ. Microbiol.* 67: 4701-4707. For each of the constructs 10-20 strains were isolated, purified and cultivated in shake flasks.

Purification of Expressed Variants

Adjust pH of the 0.22 micro m filtered fermentation sample to 4.0.

Put the sample on an ice bath with magnetic stirring. Add (NH$_4$)$_2$SO$_4$ in small aliquots (corresponding to approx. 2.0-2.2 M (NH$_4$)$_2$SO$_4$ not taking the volume increase into account when adding the compound).

After the final addition of (NH$_4$)$_2$SO$_4$, incubate the sample on the ice bath with gentle magnetic stirring for min. 45 min.

Centrifugation: Hitachi himac CR20G High-Speed Refrigerated Centrifuge equipped with R20A2 rotor head, 5° C., 20,000 rpm, 30 min.

Dissolve the formed precipitate in 200 mL 50 mM Na-acetate pH 4.0.

Filter the sample by vacuum suction using a 0.22 micro m PES PLUS membrane (IWAKI).

Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.

Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.

The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

Protazyme OL tablet/5 ml 250 mM Na-acetate pH 5.0 is dissolved by magnetic stirring (substrate: endo-protease Protazyme AK tablet from Megazyme—cat. # PRAK 11/08).

With stirring, 250 microL of substrate solution is transferred to a 1.5 mL Eppendorf tube.

25 microL of sample is added to each tube (blank is sample buffer).

The tubes are incubated on a Thermomixer with shaking (1000 rpm) at 50° C. for 15 minutes.

250 microL of 1 M NaOH is added to each tube, followed by vortexing.

Centrifugation for 3 min. at 16,100×G and 25° C.

200 microL of the supernatant is transferred to a MTP, and the absorbance at 590 nm is recorded.

TABLE 2

Relative Activity of protease variants. Numbering of substitution(s) starts from N-terminal of the mature peptide in amino acids 1 to 177 of SEQ ID NO: 3.

| | | Remaining Activity | |
|---|---|---|---|
| Variant | Substitution(s) and/or deletion(s) | 80° C. | 84° C. |
| JTP082 | ΔS5/D79L/S87P/A112P/D142L | | 53% |
| JTP091 | D79L/S87P/A112P/T124V/D142L | 43% | |
| JTP092 | ΔS5/N26R/D79L/S87P/A112P/D142L | | 60% |
| JTP095 | N26R/T46R/D79L/S87P/A112P/D142L | | 62% |
| JTP096 | T46R/D79L/S87P/T116V/D142L | | 67% |
| JTP099 | D79L/P81R/S87P/A112P/D142L | | 80% |
| JTP101 | A27K/D79L/S87P/A112P/T124V/D142L | 81% | |
| JTP116 | D79L/Y82F/S87P/A112P/T124V/D142L | 59% | |
| JTP117 | D79L/Y82F/S87P/A112P/T124V/D142L | 94% | |
| JTP127 | D79L/S87P/A112P/T124V/A126V/D142L | 53% | |

TABLE 3

Relative Activity of protease variants. Numbering of substitution(s) starts from N-terminal of the mature peptide in amino acids 1 to 177 of SEQ ID NO: 3.

| | | Relative Activity | |
|---|---|---|---|
| Variant | Substitutions | 80° C./70° C. | 85° C./70° C. |
| JTP050 | D79L S87P A112P D142L | 23% | 9% |
| JTP134 | D79L Y82F S87P A112P D142L | 40% | |
| JTP135 | S38T D79L S87P A112P A126V D142L | 62% | |
| JTP136 | D79L Y82F S87P A112P A126V D142L | 59% | |
| JTP137 | A27K D79L S87P A112P A126V D142L | 54% | |
| JTP145 | S49P D79L S87P A112P D142L | 59% | |
| JTP146 | S50P D79L S87P A112P D142L | 63% | |
| JTP148 | D79L S87P D104P A112P D142L | 64% | |
| JTP161 | D79L Y82F S87G A112P D142L | 30% | 12% |
| JTP180 | S70V D79L Y82F S87G Y97W A112P D142L | 52% | |
| JTP181 | D79L Y82F S87G Y97W D104P A112P D142L | 45% | |
| JTP187 | S70V D79L Y82F S87G A112P D142L | 45% | |
| JTP188 | D79L Y82F S87G D104P A112P D142L | 43% | |
| JTP189 | D79L Y82F S87G A112P A126V D142L | 46% | |
| JTP193 | Y82F S87G S70V D79L D104P A112P D142L | | 15% |
| JTP194 | Y82F S87G D79L D104P A112P A126V D142L | | 22% |
| JTP196 | A27K D79L Y82F S87G D104P A112P A126V D142L | | 18% |

TABLE 4

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. |
|---|---|---|
| JTP196 | A27K D79L Y82F S87G D104P A112P A126V D142L | 55% |
| JTP210 | A27K Y82F S87G D104P A112P A126V D142L | 36% |
| JTP211 | A27K D79L Y82F D104P A112P A126V D142L | 44% |
| JTP213 | A27K Y82F D104P A112P A126V D142L | 37% |

Example 3

Temperature Profile of Selected Protease Variants Using Purified Enzymes

Selected protease variants showing good thermostability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:

Mix 10 microL of 10 micro g/mL enzyme solutions and 100 microL of 0.025% zein solution in a micro titer plate (MTP).

Incubate at various temperatures for 60 min.

Add 10 microL of 100% trichloroacetic acid (TCA) solution.

Centrifuge MTP at 3500 rpm for 5 min.

Take out 15 microL to a new MTP containing 100 microL of BCA assay solution (Pierce Cat#:23225, BCA Protein Assay Kit).

Incubate for 30 min. at 60° C.

Measure A562.

The results are shown in Table 5. All of the tested protease variants showed an improved thermostability as compared to the wild type (WT) protease.

TABLE 5

Zein-BCA assay

| | Sample incubated 60 min at indicated temperatures (° C.) (micro g/mL Bovine serum albumin equivalent peptide released) | | | | | | |
|---|---|---|---|---|---|---|---|
| WT/Variant | 60° C. | 70° C. | 75° C. | 80° C. | 85° C. | 90° C. | 95° C. |
| WT | 94 | 103 | 107 | 93 | 58 | 38 | |
| JTP050 (D79L + S87P + A112P + D142L) | 86 | 101 | 107 | 107 | 104 | 63 | 36 |
| JTP077 (A27K + D79L + S87P + A112P + D142L) | 82 | 94 | 104 | 105 | 99 | 56 | 31 |
| JTP188 (D79L + Y82F + S87G + D104P + A112P + D142L) | 71 | 83 | 86 | 93 | 100 | 75 | 53 |
| JTP196 (A27K + D79L + Y82F + S87G + D104P + A112P + A126V + D142L) | 87 | 99 | 103 | 106 | 117 | 90 | 38 |

Example 4

Characterization of *Penicillium oxalicum* Glucoamylase

The *Penicillium oxalicum* glucoamylase is disclosed in SEQ ID NO: 9 herein.

Substrate. Substrate: 1% soluble starch (Sigma S-9765) in deionized water

Reaction buffer: 0.1 M Acetate buffer at pH 5.3

Glucose concentration determination kit: Wako glucose assay kit (LabAssay glucose, WAKO, Cat#298-65701).

Reaction condition. 20 microL soluble starch and 50 microL acetate buffer at pH5.3 were mixed. 30 microL enzyme solution (50 micro g enzyme protein/ml) was added to a final volume of 100 microL followed by incubation at 37° C. for 15 min.

The glucose concentration was determined by Wako kits.

All the work carried out in parallel.

Temperature optimum.

To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 6.

TABLE 6

| Temperature optimum | | | | | | | | | | |
|---|---|---|---|---|---|---|---|---|---|---|
| Temperature (° C.) | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat stability.

To assess the heat stability of the *Penicillium oxalicum* glucoamylase the Reaction condition assay was modified in that the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 7.

TABLE 7

| Heat stability | | | | | | | | | | |
|---|---|---|---|---|---|---|---|---|---|---|
| Temperature (° C.) | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH optimum.

To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 8.

TABLE 8

| pH optimum | | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.
pH stability.

To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 9.

TABLE 9

| | pH stability | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Improved Ethanol Production Process with Liquefaction at 75° C., pH 4.80

Ground corn and backset were used for this study. The dry solids (% DS) contents of the ground corn and backset were measured to be 86.78 and 7.93%, respectively, by oven drying at 105° C. for 3 hours.
Mash Preparation.

Nine different corn slurries were prepared for liquefaction. Into 5×200 g lab-o-mat canisters (Mathis, Inc.) were added 35.29 g of ground corn, 37.71 g of tap water, and 30.00 g of backset. The backset ratio was set to 30% for all slurries. Following the addition of these components, the slurries were pH-adjusted to 4.80 using 40% $H_2SO_4$ if needed. Stock solutions of all concentrated enzymes were prepared using deionized water. Aliquots of all enzymes were added to each lab-o-mat canister to reach the final concentrations specified in Table 10. Finally, deionized water was added to the slurries to ensure that the starting % DS's for all slurries were identical.

All canisters were then closed. They were placed into the lab-o-mat and the following program was used for liquefaction (Table 11):

TABLE 11

| Liquefaction: | Ramp | 5 deg/min | rpm = 30 |
|---|---|---|---|
| Lab-o-mat | Ramp time | 17 min | |
| | Liq temp | 75° C. | |
| | Liq time | 113 min | |

At the end of the program described in Table 11, all canisters were removed from the lab-o-mat and cooled immediately in an ice bath.

Fermentation Setup.

After complete cooling, urea and penicillin were added to all mashes to reach final concentrations of 750 and 3 ppm, respectively. Mashes were adjusted to pH 5.0 using 40% $H_2SO_4$ or 50% NaOH. The final % dry solids of the mashes were measured and recorded as 32.44%.

Approximately 5 g of each mash were transferred into preweighed 15 mL plastic Falcon centrifuge tubes for fermentation. A small hole was drilled into the lid of each tube to allow for $CO_2$ release during fermentation. Five replicate fermentations were prepared for each treatment. Following mash transfer, all tubes were reweighed to obtain the initial sample weights. Into each tube was then added 100 microL of rehydrated Red Star Ethanol Red yeast (rehydrated by weighing 5.5 g of dry yeast into a 150 mL Erlenmeyer flask, adding 100 mL of tap water, and stirring in a 32° C. water bath for 30 minutes), an aliquot of diluted AMG SPU glucoamylase (diluted in deionized water) needed to reach a starting concentration of 0.50 AGU/g DS. An appropriate amount of deionized water was finally added to each tube such that the total volume of liquid added to each tube relative to the sample weight was the same. All tubes were then reweighed and then placed into a preheated water bath set at 32° C. Fermentation was allowed to progress for a total of 54 hours. Tubes were vigorously vortexed after approximately 7 hours and then reweighed twice per day for the

TABLE 10

| | Amylase | Dose | Units | RSH Amylase | Dose | Units | AMG | Dose | Units | pH | Temp. | Glucoamylase | Dose | Unit |
|---|---|---|---|---|---|---|---|---|---|---|---|---|---|---|
| 1 | BAA 1407 | 1.4 | ug/gDS | | | ug/gDS | | | | 4.8 | 75 | AMG SPU | 0.5 | AGU/gDS |
| 2 | BAA 1407 | 1.4 | ug/gDS | RSH AA 96 | 3 | ug/gDS | | | | 4.8 | 75 | AMG SPU | 0.5 | AGU/gDS |
| 3 | BAA 1407 | 1.4 | ug/gDS | RSH AA 96 | 10 | ug/gDS | | | | 4.8 | 75 | AMG SPU | 0.5 | AGU/gDS |
| 4 | BAA 1407 | 1.4 | ug/gDS | RSH AA 96 | 25 | ug/gDS | | | | 4.8 | 75 | AMG SPU | 0.5 | AGU/gDS |
| 5 | BAA 1407 | 1.4 | ug/gDS | RSH AA 101 | 3 | ug/gDS | | | | 4.8 | 75 | AMG SPU | 0.5 | AGU/gDS |
| 6 | BAA 1407 | 1.4 | ug/gDS | RSH AA 101 | 10 | ug/gDS | | | | 4.8 | 75 | AMG SPU | 0.5 | AGU/gDS |
| 7 | BAA 1407 | 1.4 | ug/gDS | RSH AA 101 | 25 | ug/gDS | | | | 4.8 | 75 | AMG SPU | 0.5 | AGU/gDS |
| 8 | BAA 1407 | 1.4 | ug/gDS | RSH AA 96 | 25 | ug/gDS | AMG 001 | 10 | ug/gDS | 4.8 | 75 | AMG SPU | 0.5 | AGU/gDS |
| 9 | BAA 1407 | 1.4 | ug/gDS | RSH AA 101 | 25 | ug/gDS | AMG 001 | 10 | ug/gDS | 4.8 | 75 | AMG SPU | 0.5 | AGU/gDS | remaining fermentation time. The grams of ethanol produced per gram of dry solids in each tube was calculated from the weight loss data according to the following equation:

$$\text{g ethanol/g } DS = \frac{\text{g } CO_2 \text{ weight loss} \times \frac{1 \text{ mol } CO_2}{44.0098 \text{ g } CO_2} \times \frac{1 \text{ mol ethanol}}{1 \text{ mol } CO_2} \times \frac{46.094 \text{ g ethanol}}{1 \text{ mol ethanol}}}{(\text{g corn in tube} \times \% \ DS \text{ of corn})}$$

Three of the replicate tubes were pulled after 54 hours of fermentation for HPLC analysis. Pulled samples were treated with 50 microL of 40% $H_2SO_4$ to stop fermentation and vortexed thoroughly. The samples were then centrifuged at 1570×g for 10 minutes and then filtered into HPLC vials through 0.45 micro m syringe filters. HPLC analysis was finally conducted on the samples to quantify the amounts of DP4+, DP3, DP2, glucose, fructose, lactic and acetic acids, glycerol, and ethanol.

Results

FIG. 1 shows the averaged HPLC results obtained for the treatments after 54 hours of fermentation. A significant increase in ethanol production was measured when RSH AA 96, RSH AA 101, and AMG 001 glucoamylase were added into liquefaction on top of BAA 1407 alpha amylase.

The Present Invention is Described in the Following Paragraphs:

Paragraph 1. A process for producing fermentation products from starch-containing material comprising the steps of:
 i) liquefying the starch-containing material at a temperature in the range from 60-80° C. using:
  a bacterial alpha-amylase;
  a raw starch hydrolyzing alpha-amylase;
  a carbohydrate-source generating enzyme having a heat stability at 70° C., pH 5.3, of at least 70%;
 ii) saccharifying using a carbohydrate-source generating enzyme;
 iii) fermenting using a fermenting organism.

Paragraph 2. The process of paragraph 1, further comprises, prior to the liquefaction step i), the steps of:
 a) reducing the particle size of the starch-containing material, preferably by dry milling;
 b) forming a slurry comprising the starch-containing material and water.

Paragraph 3. The process of paragraph 1 or 2, wherein at least 50%, preferably at least 70%, more preferably at least 80%, especially at least 90% of the starch-containing material fit through a sieve with #6 screen.

Paragraph 4. The process of any of paragraphs 1-3, wherein the pH during liquefaction step i) is in the range from 4-6, preferably from 4.5-5.0 or between 4.5-4.8 or between 5.0 and 6.0.

Paragraph 5. The process of any of paragraphs 1-4, wherein the temperature during liquefaction is in the range between from 70-80° C. such as 75-80° C., preferably around 75° C.

Paragraph 6. The process of any of paragraphs 1-5, wherein liquefaction is carried out for 0.1-10 hours, such as 1-3 hours, such as around 1.5 hours.

Paragraph 7. The process of paragraph 6, wherein a jet-cooking step is carried out after liquefaction in step i), such as wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.

Paragraph 8. The process of any of paragraphs 1-7, wherein saccharification and fermentation is carried out sequentially or simultaneously.

Paragraph 9. The process of any of paragraphs 1-8, wherein saccharification is carried out at a temperature from 20-75° C., preferably from 40-70° C., such as around 60° C., and at a pH between 4 and 5, such as around pH 4.5.

Paragraph 10. The process of any of paragraphs 1-9, wherein fermentation or simultaneous saccharification and fermentation (SSF) is carried out at a temperature from 25° C. to 40° C., such as from 28° C. to 35° C., such as from 30° C. to 34° C., preferably around about 32° C., wherein fermentation is ongoing for 6 to 120 hours, in particular 24 to 96 hours.

Paragraph 11. The process of any of paragraphs 1-10, wherein the fermentation product is an alcohol, preferably ethanol, especially fuel ethanol, potable ethanol and/or industrial ethanol.

Paragraph 12. The process of any of paragraphs 1-11, wherein the fermentation product is recovered after fermentation, such as by distillation.

Paragraph 13. The process of any of paragraphs 1-12, wherein the starch-containing starting material is whole grains.

Paragraph 14. The process of any of paragraphs 1-13, wherein the starch-containing material is derived from corn, wheat, barley, rye, milo, sago, cassava, manioc, tapioca, sorghum, rice or potatoes.

Paragraph 15. The process of any of paragraphs 1-14, wherein the fermenting organism is yeast, preferably a strain of *Saccharomyces*.

Paragraph 16. The process of any of paragraphs 1-15, wherein the fermenting organism is a strain of *Saccharomyces cerevisae*.

Paragraph 17. The process of paragraphs 1-16, wherein the bacterial alpha-amylase is derived from a strain of *Bacillus* (also referred to as *Geobacillus*).

Paragraph 18. The process of paragraph 17, wherein the bacterial alpha-amylase is of the genus *Bacillus* or *Geobacillus*, such as a strain of *Bacillus stearothermophilus*, in particular a variant of a *Bacillus stearothermophilus* alpha-amylase or *Geobacillus stearothermophilus*, such as the one shown in SEQ ID NO: 3 in WO 99/019467 or SEQ ID NO: 1 herein, in particular the *Bacillus stearothermophilus* alpha-amylase is truncated, preferably to have 491 amino acids.

Paragraph 19. The process of any of paragraphs 1-18, wherein the bacterial alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

Paragraph 20. The process of any of paragraphs 17-19, wherein the bacterial alpha-amylase has a T½ (min) at pH 4.5, 75° C., 0.12 mM $CaCl_2$) of at least 20, such as at least 25, such as at least 30, such as at least 40, such as at least 50, such as at least 60, such as at least 70, such as at least 80, such as at least 90, such as at least 100, such as at least 110, such as at least 120, such as at least 130, such as at least 140, such as at least 150, such as at least 160, such as at least 170, such as at least 180 such as between 20-300, such as between 50-300, such as between 60-300, such as between 70-300, such as between 80-300, such as between 90-300, such as between 100-300, such as between 120-300, such as between 140-300 such as between 160-300, such as between 180-300.

Paragraph 21. The process of any of paragraphs 17-20, wherein the bacterial alpha-amylase is derived from *Bacillus stearothermophilus* alpha-amylase truncated to have 491 amino acids with mutations selected from the group consisting of:

V59A+Q89R+E129V+K177L+R179E+I181*+G182*+N193F+H208Y+K220P+N224L+Q254S;
E129V+K177L+R179E+I181*+G182*+N193F; and
E129V+K177L+R179E+I181*+G182*+N193F+K220P+N224L+S242Q+Q254S.

Paragraph 22. The process of any of paragraphs 17-21, wherein the *Bacillus stearothermophilus* or *Geobacillus stearothermophilus* alpha-amylase is a variant with the following mutations: I181*+G182*, preferably I181*+G182*+N193F using SEQ ID NO: 3 in WO 99/019467 or SEQ ID NO: 1 herein for the numbering.

Paragraph 23. The process of paragraph 1, wherein the bacterial alpha-amylase is a chimeric alpha-amylase disclosed in Richardson et al., 2002, *The Journal of Biological Chemistry* 277(29): 26501-26507, preferably the one referred to as BD5088 or shown as amino acids 1 to 435 of SEQ ID NO: 2 in WO 2007/134207.

Paragraph 24. The process of paragraphs 1-23, wherein the raw starch hydrolyzing alpha-amylase is of fungal origin, preferably a variant of *Rhizomucor pusillus* alpha-amylase with *Aspergillus niger* glucoamylase linker and SBD and further one or more of the following substitutions: G128D, D143N, K192R, such as G128D+D143N or G128D+D143N+K192R (using SEQ ID NO: 14 herein for the numbering).

Paragraph 25. The process of any of paragraphs 1-24, further wherein the carbohydrate-source generating enzyme present and/or added during liquefaction step i) is a glucoamylase.

Paragraph 26. The process of paragraph 25, wherein the carbohydrate-source generating enzyme is a glucoamylase having a heat stability at 70° C., pH 5.3, of at least 75%, preferably at least 80%, preferably at least 85%.

Paragraph 27. The process of paragraph 25 or 26, wherein the carbohydrate-generating enzyme is a glucoamylase having a relative activity at pH 4.5 of at least 80%, preferably at least 85%, preferably at least 90%.

Paragraph 28. The process of any of paragraphs 25-27, wherein the carbohydrate-generating enzyme is a glucoamylase having a pH stability at pH 4.5 of at least at least 80%, at least 85%, at least 90%, at least 95%, at least 100%.

Paragraph 29. The process of any of paragraphs 25-28, wherein the carbohydrate-source generating enzyme is a glucoamylase, preferably derived from a strain of the genus *Penicillium*, especially a strain of *Penicillium oxalicum* disclosed as SEQ ID NO: 2 in PCT/CN10/071,753 published as WO 2011/127802 or SEQ ID NO: 9 and 15 herein, or a variant thereof having a K79V substitution (using SEQ ID NO: 15 herein for numbering).

Paragraph 30. The process of any of paragraphs 25-29, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071,753 published as WO 2011/127802 or SEQ ID NO: 9 herein.

Paragraph 31. The process of any of paragraphs 1-30, further wherein a glucoamylase is present and/or added during saccharification and/or fermentation.

Paragraph 32. The process of any of paragraphs 1-31, wherein the glucoamylase present and/or added during saccharification and/or fermentation is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*.

Paragraph 33. The process of any of paragraphs 1-32, further wherein a protease is present or added during liquefaction.

Paragraph 34. The process of paragraph 33, wherein the protease is of fungal or bacterial origin.

Paragraph 35. The process of paragraph 33 or 34, wherein the protease has a thermostability value of more than 20% determined as Relative Activity at 80° C./70° C.

Paragraph 36. The process of any of paragraphs 33-35, wherein the protease has a thermostability value of more than 30%, more than 40%, more than 50%, more than 60%, more than 70%, more than 80%, more than 90% determined as Relative Activity at 80° C./70° C.

Paragraph 37. The process of any of paragraphs 33-36, wherein the protease is a metallo protease.

Paragraph 38. The process of any of paragraphs 33-37, wherein the protease is a variant of the metallo protease derived from a strain of the genus *Thermoascus*, preferably a strain of *Thermoascus aurantiacus*, especially *Thermoascus aurantiacus* CGMCC No. 0670.

Paragraph 39. The process of any of paragraphs 33-38, wherein the protease is a variant of the metallo protease disclosed as the mature part of SEQ ID NO. 2 disclosed in WO 2003/048353 or the mature part of SEQ ID NO: 1 in WO 2010/008841 or SEQ ID NO: 3 herein.

Paragraph 40. The process of any of paragraphs 33-39, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO. 1 in WO 2010/008841 or SEQ ID NO: 3 herein.

Paragraph 41. The process of any of paragraphs 33-40, wherein the protease is derived from a strain of *Pyrococcus*.

Paragraph 42. The process of any of paragraphs 33-41, wherein the protease is derived from a strain of *Pyrococcus furiosus*.

Paragraph 43. The process of any of paragraphs 33-42 wherein the protease is the one shown in SEQ ID NO: 1 in U.S. Pat. No. 6,258,726 or SEQ ID NO: 13 herein.

Paragraph 44. The process of any of paragraphs 33-43, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,258,726 or SEQ ID NO: 13 herein.

Paragraph 45. The process of any of paragraphs 1-44, further wherein a pullulanase is present during liquefaction and/or saccharification.

Paragraph 46. A composition comprising
a bacterial alpha-amylase;
a raw starch hydrolyzing alpha-amylase;

a carbohydrate-source generating enzyme having a heat stability at 70° C., pH 5.3, of at least 70%.

Paragraph 47. The composition of paragraph 46, wherein the alpha-amylase is derived from a strain of the genus *Bacillus*, such as a strain of *Bacillus stearothermophilus* or *Geobacillus stearothermophilus*, in particular a variant of a *Bacillus stearothermophilus* or *Bacillus stearothermophilus* alpha-amylase, such as the one shown in SEQ ID NO: 3 in WO 99/019467 or SEQ ID NO: 1 herein.

Paragraph 48. The composition of paragraph 46 or 47, wherein the *Bacillus stearothermophilus* or *Geobacillus stearothermophilus* alpha-amylase is a variant with the following mutations: I181*+G182*, preferably I181*+G182*+N193F using SEQ ID NO: 3 in WO 99/019467 or SEQ ID NO: 1 herein for the numbering.

Paragraph 49. The composition of any of paragraphs 46-48, wherein *Bacillus stearothermophilus* or *Geobacillus stearothermophilus* alpha-amylase is truncated to have around 491 amino acids.

Paragraph 50. The composition of any of paragraphs 46-49, wherein the bacterial alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

Paragraph 51. The composition of any of paragraphs 46-50, wherein the alpha-amylase has a T½ (min) at pH 4.5, 75° C., 0.12 mM CaCl$_2$) of at least 20, such as at least 25, such as at least 30, such as at least 40, such as at least 50, such as at least 60, such as at least 70, such as at least 80, such as at least 90, such as at least 100, such as at least 110, such as at least 120, such as at least 130, such as at least 140, such as at least 150, such as at least 160, such as at least 170, such as at least 180 such as at between 20-300, such as between 50-300, such as between 60-300, such as between 70-300, such as between 80-300, such as between 90-300, such as between 100-300, such as between 120-300, such as between 140-300 such as between 160-300, such as between 180-300.

Paragraph 52. The composition of any of paragraphs 46-51, wherein the bacterial alpha-amylase is derived from *Bacillus stearothermophilus* alpha-amylase truncated to have around 491 amino acids with the mutations selected from the group consisting of:

V59A+Q89R+E129V+K177L+R179E+I181*+G182*+N193F+H208Y+K220P+N224L+Q254S;

E129V+K177L+R179E+I181*+G182*+N193F; and

E129V+K177L+R179E+I181*+G182*+N193F+K220P+N224L+S242Q+Q254S.

Paragraph 53. The composition of any of paragraphs 46-52, wherein the raw starch hydrolyzing alpha-amylase is of fungal origin, preferably a variant of *Rhizomucor pusillus* alpha-amylase with *Aspergillus niger* glucoamylase linker and SBD and further one or more of the following substitutions: G128D, D143N, K192R, such as G128D+D143N or G128D+D143N+K192R (using SEQ ID NO: 14 herein for the numbering).

Paragraph 54. The composition of any of paragraphs 46-53, wherein the carbohydrate-source generating enzyme is a glucoamylase, preferably a glucoamylase having a heat stability at 70° C., pH 5.3, of at least 75%, preferably at least 80%, preferably at least 85%.

Paragraph 55. The composition of any of paragraphs 46-54, wherein the carbohydrate-generating enzyme is a glucoamylase having a relative activity at pH 4.5 of at least 80%, preferably at least 85%, preferably at least 90%.

Paragraph 56. The composition of any of paragraphs 46-55, wherein the carbohydrate-generating enzyme is a glucoamylase having a pH stability at pH 4.5 of at least at least 80%, at least 85%, at least 90%, at least 95%, at least 100%.

Paragraph 57. The composition of any of paragraphs 46-56, wherein the carbohydrate-source generating enzyme is a glucoamylase, preferably derived from a strain of the genus *Penicillium*, especially a strain of *Penicillium oxalicum* disclosed as SEQ ID NO: 2 in PCT/CN10/071,753 published as WO 2011/127802 or SEQ ID NO: 9 and 15 herein, or a variant thereof having a K79V substitution (using SEQ ID NO: 15 herein for numbering).

Paragraph 58. The composition of paragraph 46-57, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071,753 published as WO 2011/127802 or SEQ ID NO: 9 herein.

Paragraph 59. The composition of any of paragraphs 46-58, further comprising a protease.

Paragraph 60. The composition of any of paragraphs 46-59, further comprising a metallo protease.

Paragraph 61. The composition of any of paragraphs 46-60, wherein the protease has a thermostability of more than 30%, more than 40%, more than 50%, more than 60%, more than 70%, more than 80%, more than 90% determined as Relative Activity at 80° C./70° C.

Paragraph 62. The composition of any of paragraphs 46-61, wherein the protease has a thermostability of more than 12%, more than 14%, more than 16%, more than 18%, more than 20%, determined as Relative Activity at 85° C./70° C.

Paragraph 63. The composition of any of paragraphs 46-62, wherein the protease is a variant of the metallo protease derived from *Thermoascus aurantiacus* CGMCC No. 0670 shown in SEQ ID NO: 3 herein.

Paragraph 64. The composition of any of paragraphs 46-63, wherein the protease is derived from a strain of *Pyrococcus*

Paragraph 65. The composition of any of paragraphs 46-64, wherein the protease is derived from a strain of *Pyrococcus furiosus*.

Paragraph 66. The process of any of paragraphs 46-65 wherein the protease is the one shown in SEQ ID NO: 1 in U.S. Pat. No. 6,258,726 or SEQ ID NO: 13 herein.

Paragraph 67. The process of any of paragraphs 46-66, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,258,726 or SEQ ID NO: 13 herein.

Paragraph 68. The composition of any of paragraphs 46-67, further comprising a pullulanase.

Paragraph 69. The composition of any of paragraphs 46-68 comprising a bacterial alpha-amylase derived from *Bacillus stearothermophilus;* a raw starch hydrolyzing alpha-amylase derived from *Rhizomucor pusillus;* a carbohydrate-source generating enzyme having a heat stability at 70° C., pH 5.3, of at least 70% derived from *Penicillium oxalicum.*

The invention claimed is:

1. A process for producing a fermentation product comprising the steps of:
   (a) liquefying a starch-containing material at a temperature in the range from 60-80° C. by contacting said starch-containing material with:
      a bacterial alpha-amylase having at least 90% sequence identity to the amino acid sequence of SEQ ID NO: 1, wherein said bacterial alpha-amylase has alpha-amylase activity;
      a raw starch hydrolyzing alpha-amylase having at least 90% sequence identity to the amino acid sequence of SEQ ID NO:14 which includes one or more amino acid substitutions selected from the group consisting of: G128D, D143N, K192R, and a combination thereof, wherein said raw starch hydrolyzing alpha-amylase has alpha amylase activity;
      a glucoamylase having at least 95% sequence identity to the mature polypeptide of the amino acid sequence of SEQ ID NO: 9 which includes a K79V substitution, wherein said glucoamylase has glucoamylase activity and has a heat stability at 70° C., pH 5.3, of at least 70%;
      to produce a liquefied starch-containing material;
   (b) saccharifying said liquefied starch-containing material in the presence of a carbohydrate-source generating enzyme to produce a saccharified starch-containing material; and
   (c) fermenting said saccharified starch-containing material in the presence of a fermenting organism to produce said fermentation product.

2. The process of claim 1, wherein said fermentation product is an alcohol.

3. The process of claim 1, wherein said bacterial alpha-amylase is a *Bacillus* alpha-amylase.

4. The process of claim 1, wherein said raw starch hydrolyzing alpha-amylase is a variant of *Rhizomucor pusillus* alpha-amylase having at least 90% sequence identity to the amino acid sequence of SEQ ID NO: 14 with a *Aspergillus niger* glucoamylase linker and a starch binding domain, wherein said raw starch hydrolyzing alpha-amylase comprises one or more of the following substitutions selected from the group consisting of: G128D, D143N, K192R, G128+D143N, and G128D+D143N+K192N, and wherein said raw starch hydrolyzing alpha-amylase has alpha-amylase activity.

5. The process of claim 1, wherein said glucoamylase is a glucoamylase having a heat stability at 70° C., pH 5.3, of at least 75%.

6. The process of claim 1, wherein said glucoamylase is a glucoamylase having a relative activity at pH 4.5 of at least 80%.

7. The process of claim 1, wherein said glucoamylase has a pH stability at pH 4.5 of at least 80%.

8. The process of claim 1, wherein the glucoamylase has at least 97% sequence identity to the mature polypeptide set forth in the amino acid sequence of SEQ ID NO: 9.

9. The process of claim 1, further wherein a protease is present or added during said liquefying step (a).

10. The process of claim 1, further wherein a pullulanase is present during said liquefying step (a) and/or said saccharifying step (b).

11. A process for producing a fermentation product comprising the steps of:
    (a) liquefying a starch-containing material at a temperature in the range from 60-80° C. by contacting said starch-containing material with:
       a bacterial alpha-amylase having at least 90% sequence identity to the amino acid sequence of SEQ ID NO: 1, wherein said bacterial alpha-amylase has alpha-amylase activity;
       a raw starch hydrolyzing alpha-amylase having at least 90% sequence identity to the amino acid sequence of SEQ ID NO: 14 which includes one or more amino acid substitutions selected from the group consisting of: G128D, D143N, K192R, and a combination thereof, wherein said raw starch hydrolyzing alpha-amylase has alpha amylase activity;
       a glucoamylase variant comprising the amino acid sequence of SEQ ID NO: 9 or SEQ ID NO: 15 which includes a K79V substitution, wherein said glucoamylase variant has glucoamylase activity and further has a heat stability at 70° C., pH 5.3, of at least 70%;
       to produce a liquefied starch-containing material;
    (b) saccharifying said liquefied starch-containing material in the presence of a carbohydrate-source generating enzyme to produce a saccharified starch-containing material; and
    (c) fermenting said saccharified starch-containing material in the presence of a fermenting organism to produce said fermentation product.

12. The process of claim 11, wherein said liquefying step (a) is at a temperature in the range from 70-80° C.

13. The process of claim 12, wherein said steps (b) and (c) occur simultaneously.

14. A process for producing a fermentation product comprising the steps of:
    (a) liquefying a starch-containing material at a temperature in the range from 60-80° C. by contacting said starch-containing material with:
       a bacterial alpha-amylase having at least 90% sequence identity to the amino acid sequence of SEQ ID NO: 1, wherein said bacterial alpha-amylase has alpha-amylase activity;
       a raw starch hydrolyzing alpha-amylase having at least 90% sequence identity to the amino acid sequence of SEQ ID NO: 14 which includes one or more amino acid substitutions selected from the group consisting of: G128D, D143N, K192R, and a combination thereof, wherein said raw starch hydrolyzing alpha-amylase has alpha amylase activity;
       a glucoamylase having at least 90% sequence identity to the amino acid sequence of SEQ ID NO: 9 which includes a K79V substitution, wherein said glucoamylase variant has glucoamylase activity;
    (b) saccharifying said liquefied starch-containing material in the presence of a carbohydrate-source generating enzyme to produce a saccharified starch-containing material; and
    (c) fermenting said saccharified starch-containing material in the presence of a fermenting organism to produce said fermentation product.

15. The process of claim 11, wherein said liquefying step (a) is at a temperature in the range from 70-80° C.

16. The process of claim 12, wherein said steps (b) and (c) occur simultaneously.

* * * * *

UNITED STATES PATENT AND TRADEMARK OFFICE
CERTIFICATE OF CORRECTION

PATENT NO. : 9,677,095 B2
APPLICATION NO. : 14/351471
DATED : June 13, 2017
INVENTOR(S) : Deinhammer et al.

Page 1 of 1

It is certified that error appears in the above-identified patent and that said Letters Patent is hereby corrected as shown below:

On the Title Page

Item (56) References cited - Foreign Patent Documents:
Please delete "DK 10 2005 062984 A1 7/2007" and insert -- DE 10 2005 062984 A1 7/2007 --

Signed and Sealed this
Seventeenth Day of October, 2017

Joseph Matal
*Performing the Functions and Duties of the
Under Secretary of Commerce for Intellectual Property and
Director of the United States Patent and Trademark Office*